United States Patent
Matsuda et al.

(10) Patent No.: US 6,813,303 B2
(45) Date of Patent: Nov. 2, 2004

(54) LASER OSCILLATOR AND LIGHT SCATTERING PARTICLE DETECTOR USING THE SAME

(75) Inventors: Tomonobu Matsuda, Tokyo (JP); Takashi Minakami, Tokyo (JP); Kenji Sasaki, Tokyo (JP); Tsutomu Nakajima, Tokyo (JP)

(73) Assignee: Rion Co., Ltd., Tokyo (JP)

( * ) Notice: Subject to any disclaimer, the term of this patent is extended or adjusted under 35 U.S.C. 154(b) by 0 days.

(21) Appl. No.: 10/057,779

(22) Filed: Jan. 24, 2002

(65) Prior Publication Data

US 2004/0011974 A1 Jan. 22, 2004

(30) Foreign Application Priority Data

Jan. 24, 2001 (JP) ........................................ 2001-016168

(51) Int. Cl.[7] .............................................. H01S 3/094
(52) U.S. Cl. .......................... 372/75; 372/69; 356/337; 356/340
(58) Field of Search ............................ 372/98, 101, 69, 372/75; 356/337, 340

(56) References Cited

U.S. PATENT DOCUMENTS 5,583,635 A * 12/1996 Miura et al. ................ 356/338
6,111,642 A * 8/2000 DeFreez et al. ............ 356/337

FOREIGN PATENT DOCUMENTS

| JP | 02-052237 P | | 2/1990 | |
| JP | 2052237 | * | 2/1990 | .......... G01N/15/14 |

* cited by examiner

Primary Examiner—Don Wong
Assistant Examiner—Leith A Al-Nazer
(74) Attorney, Agent, or Firm—Carrier, Blackman & Associates, P.C.; Joseph P. Carrier; William D. Blackman

(57) ABSTRACT

According to the present invention, there is provided a light scattering type particle detector, using a semiconductor laser as a light source, for detecting particles contained in sample fluid which defines a flow path, wherein laser light generated from the semiconductor laser is irradiated to irradiate a region of the flow path with a concave mirror and thereby a particle detecting region is defined.

According to the present invention, there is also provided a laser oscillator wherein the optical axis of a semiconductor laser for generating pumping laser light has a predetermined angle with respect to the optical axis of a laser medium for irradiating laser light by pumping. Using such a laser oscillator, laser light irradiated from the laser oscillator is condensed to irradiate a region of a flow path defined by sample fluid, and thereby a particle detecting region is defined. Particles contained in the particle detecting region are detected by receiving scattered light with a light receiving portion.

13 Claims, 14 Drawing Sheets

PRIOR ART

LASER OSCILLATOR AND LIGHT SCATTERING PARTICLE DETECTOR USING THE SAME

BACKGROUND OF THE INVENTION

1. Field of the Invention

The present invention relates to a laser oscillator using a semiconductor laser, and a light scattering type particle detector for detecting particles contained in sample fluid using the laser oscillator.

2. Description of the Prior Art

In a conventional light scattering type particle detector as shown in FIG. 22, a laser oscillator comprises a laser medium 200 and a reflecting mirror 201, and a flow path 202 defined by fluid to be detected is provided between the laser medium 200 and the reflecting mirror 201. Pumping laser light Le emitted from a semiconductor laser 203 is condensed with a condenser lens 204 to irradiate upon the laser medium 200, and thereby the laser medium 200 is pumped. A particle detecting region 205 is a region where laser light La resonating between the laser medium 200 and the reflecting mirror 201 intersects the flow path 202. Scattered light Ls being a scattered portion of the resonating laser light La in the particle detecting region 205 is received at a light receiving portion 206. Particles contained in sample fluid are detected by electrical signals generated based on the intensity of the scattered light Ls which is received.

Further, in the prior art as disclosed in Japanese Patent Publication No. 6-58318, an antireflection coating through which the pumping wavelength of the semiconductor laser 203 (the pumping wavelength of the laser medium 200) can penetrate and a high reflection coating having a characteristic of reflecting the oscillating wavelength of the laser medium 200 are applied onto the surface of the laser medium 200 opposite to the condenser lens 204.

The conventional light scattering type particle detector as shown in FIG. 22 has a drawback that the pumping laser light Le is incident on the semiconductor laser 203 as feedback light even with the antireflection coating through which the pumping wavelength of the semiconductor laser 203 can penetrate. Another drawback exists wherein the laser light La resonating between the laser medium 200 and the reflecting mirror 201 penetrates through the laser medium 200 so as to be incident on the semiconductor laser 203 as feedback light even with the high reflection coating having a characteristic of reflecting the oscillating wavelength of the laser medium 200. Such feedback light causes fluctuation to the intensity of the pumping laser light Le emitted from a semiconductor laser 203 and the resonating laser light La and such fluctuation deteriorates the signal/noise ratio. It is acknowledged that when laser light emitted from the semiconductor laser is later incident on the semiconductor laser again because of reflection or the like, such feedback light causes fluctuation noise.

In another conventional light scattering type particle detector as shown in FIG. 23, a laser oscillator comprises a laser medium 215 and a reflecting mirror 216, and a flow path 217 defined by fluid to be detected is provided between the laser medium 215 and the reflecting mirror 216. Pumping laser light Le emitted from a semiconductor laser 218 is condensed with a condenser lens 219 to irradiate upon the laser medium 215, and thereby the laser medium 215 is pumped. A particle detecting region 220 is a region where laser light La resonating between the laser medium 215 and the reflecting mirror 216 intersects the flow path 217. A scattered portion of the resonating laser light La in the particle detecting region 220 is received at a light receiving portion (not shown in the drawing). Particles contained in the sample fluid are detected by electrical signals generated based on the intensity of the scattered light which is received.

A case is comprised of a hollow first setting block 222 and a hollow second setting block 223. The laser medium 215 is fixed to the second setting block 223 and the second setting block 223 is fixed to the first setting block 222. A light receiving case (not shown in the drawing) for housing the light receiving portion is fixed to the side surface of the first setting block 222.

If there is no error in the fixation of the laser medium 215 to the second setting block 223 or the like, laser light La irradiated from the laser medium 215 goes in the perpendicular direction with respect to the end surface (irradiation surface) of the laser medium 215 and in the direction corresponding to the core axis of the first setting block 222.

However, in fact, error arises in the fixation of the laser medium 215 to the second setting block 223, and resultantly the laser light La is not oriented to travel in the direction corresponding to the core axis of the first setting block 222. In this case, it is necessary to adjust the setting angle of the reflecting mirror 216 with respect to the first setting block 222 so that the laser light La reflected by the reflecting mirror 216 can reflect accurately to the laser medium 215.

Further, even if the setting angle of the reflecting mirror 216 is adjusted to be the most preferable angle to make the laser light La reflected by the reflecting mirror 216 reflect accurately to the laser medium 215, the irradiating direction of the oscillated laser light La does not coincide with the core axis of the first setting block 222. Therefore, it may be necessary to shift the flow path 217 which is positioned on the assumption that the irradiating direction of the oscillated laser light La coincides with the core axis of the first setting block 222. The shift of the flow path 217 changes the position of the particle detecting region 220. Depending on this, it is necessary to adjust the setting position of the light receiving case for housing the light receiving portion with respect to the first setting block 222.

Accordingly, the conventional light scattering type particle detector exhibits drawbacks including that complicated adjustment is required for the position adjustment of the flow path 217 and the setting adjustment of the light receiving case with respect to the first setting block 222, and that a lot of work is also required for the assembly of the whole apparatus, including tasks such as setting the angle adjustment of the reflecting mirror 216 in the case where there is error in the fixation.

Further, as other light scattering type particle detectors, two types as disclosed in Japanese Patent Publication No. 6-58318 are known. One type uses a He—Ne gas laser as a laser medium and the other uses a solid-state laser as a laser medium.

In either type, a flow path 232 defined by sample fluid flowing from an inlet 230 to an outlet 231 is provided within a laser resonator as shown in FIG. 24. A particle detecting region 233 is a region where laser light La having a circular transverse mode pattern intersects the flow path 232.

Recently, there is a tendency that electronic devices of high precision are manufactured in clean surroundings such as a clean room. The number of particles suspending within a clean room is controlled so as to ensure the cleanness of the clean room. It is required that a large volume of sample air is taken into a particle detector for controlling the number of particles in the clean room.

Therefore, it is necessary to increase the cross section of a flow path for flowing a large volume of sample air through the flow path within a predetermined period of time. Also, it is necessary to increase the cross section of laser light in accordance with the cross section of the flow path and thereby define a larger particle detecting region for detecting all particles within sample air passing the flow path.

However, if the cross section of laser light is increased in the conventional light scattering type particle detector, the following problems are caused:

(1) In a light scattering type particle detector using He—Ne gas laser as a laser medium, a He—Ne laser medium is comprised of a capillary glass tube having a circular cross section and thereby the transverse mode pattern of laser light is made circular. If such a circular cross section of laser light is broadened, the energy density is decreased and the amount of scattered light is decreased. Therefore, it is difficult to detect fine particles.

(2) In a light scattering type particle detector using a solid-state laser as a laser medium, the surface of the irradiating lens of a pumping light source and the surface of the reflecting mirror are formed to have a spherical shape and thereby the transverse mode pattern of laser light is made circular. If such a circular cross section of laser light is broadened, the energy density is decreased and the amount of scattered light is decreased. Therefore, it is difficult to detect fine particles with accuracy.

(3) In the conventional art, for defining a larger particle detecting region without reducing the energy density, it is necessary to use a laser medium having a longer and thicker glass tube in the case of He—Ne gas laser. Also, it is necessary to use a pumping light source having a high output in the case of a solid-state laser. In both cases, a large-scale device and high costs are required.

Further, since the cross section of laser light expands circularly, the volume of a particle detecting region is increased and scattered light generated by air molecules in the detecting region is increased. Therefore, the increase of noise is caused by the increase of such background light and it becomes difficult to detect fine particles with accuracy.

SUMMARY OF THE INVENTION

For solving the above-mentioned drawbacks, according to an aspect of the present invention, there is provided a laser oscillator in which laser light is irradiated by pumping a laser medium using pumping laser light generated from a semiconductor laser, wherein the pumping laser light generated from the semiconductor laser is condensed to irradiate upon the laser medium with a concave mirror and the core axis (chief ray) of the pumping laser light which is reflected on the concave mirror has a predetermined angle with respect to the optical axis of the laser medium.

With this, since the pumping laser light generated from the semiconductor laser is condensed to irradiate upon the laser medium with the concave mirror and the core axis (chief ray) of the pumping laser light which is reflected on the concave mirror has a predetermined angle with respect to the optical axis of the laser medium, it is possible to prevent the pumping laser light from irradiating back upon the semiconductor laser, prevent fluctuation in the intensity of the pumping laser light, and thereby reduce any fluctuation in the intensity of the laser light which is irradiated from the laser medium.

According to another aspect of the present invention, a light scattering type particle detector, using a semiconductor laser as a light source, for detecting particles contained in sample fluid which defines a flow path, wherein laser light generated from the semiconductor laser is irradiated upon the flow path with a concave mirror and thereby a particle detecting region is defined.

With this, since laser light generated from the semiconductor laser is condensed with the concave mirror and the laser light is allowed to irradiate the particle detecting region, it is possible to prevent the laser light generated from the semiconductor laser from irradiating back upon the semiconductor laser and thereby to reduce the fluctuation in the intensity of the laser light generated from the semiconductor laser. Therefore, it is possible to accurately detect particles having a relatively small diameter.

According to another aspect of the present invention, a light scattering type particle detector, using a semiconductor laser as a light source, for detecting particles contained in sample fluid which defines a flow path, wherein laser light generated from the semiconductor laser is condensed to irradiate upon the flow path with a concave mirror and a condenser lens, and thereby a particle detecting region is defined, and wherein the core axis (chief ray) of the laser light which is reflected on the concave mirror has a predetermined angle with respect to the optical axis of the condenser lens.

With this, since laser light generated from the semiconductor laser is reflected on a concave mirror and condensed with a condenser lens, and thereby the particle detecting region is irradiated, and also the core axis (chief ray) of the laser light which is reflected on the concave mirror has a predetermined angle with respect to the optical axis of the condenser lens, it is possible to prevent the laser light generated from the semiconductor laser from irradiating back upon the semiconductor laser and thereby to reduce the fluctuation in the intensity of the laser light generated from the semiconductor laser. Therefore, it is possible to accurately detect particles having a relatively small diameter.

According to another aspect of the present invention, there is provided a light scattering type particle detector in which a laser medium is pumped by pumping laser light generated from a semiconductor laser, laser light irradiated from the laser medium is irradiated to a flow path defined by sample fluid whereby a particle detecting region is defined, particles contained in the particle detecting region are detected, wherein the pumping laser light generated from the semiconductor laser is condensed to irradiate upon the laser medium with a concave mirror and the core axis (chief ray) of the pumping laser light which is reflected on the concave mirror has a predetermined angle with respect to the optical axis of the laser medium.

With this, since the pumping laser light generated from the semiconductor laser is condensed to irradiate upon the laser medium with a concave mirror and the core axis (chief ray) of the pumping laser light which is reflected on the concave mirror has a predetermined angle with respect to the optical axis of the laser medium, it is possible to prevent the pumping laser light from irradiating back upon the semiconductor laser, to prevent the fluctuation in the intensity of the pumping laser light, and thereby to reduce the fluctuation in the intensity of the laser light irradiated from the laser medium. Therefore, it is possible to accurately detect particles having a relatively small diameter.

According to another aspect of the present invention, there is provided a laser oscillator in which pumping laser light generated from a semiconductor laser is condensed to irradiate upon a laser medium with a condenser lens, the laser medium is pumped, and thereby laser light is irradiated, wherein the optical axis of the semiconductor laser has a predetermined angle with respect to the optical axis of the laser medium.

With this, since the optical axis of the semiconductor laser has a predetermined angle with respect to the optical axis of the laser medium, it is possible to prevent the pumping laser light from irradiating back upon the semiconductor laser, to prevent the fluctuation in the intensity of the pumping laser light, and thereby to reduce the fluctuation in the intensity of the laser light irradiated from the laser medium.

According to another aspect of the present invention, there is provided a light scattering type particle detector in which the laser light irradiated from the above-mentioned laser oscillator is irradiated to a flow path defined by sample fluid, and thereby a particle detecting region is defined, particles contained wherein being detected by receiving scattered light generated by the laser light.

With this, since the optical axis of the semiconductor laser has a predetermined angle with respect to the optical axis of the laser medium, it is possible to prevent the pumping laser light from irradiating back upon the semiconductor laser, to prevent the fluctuation in the intensity of the pumping laser light, and thereby to reduce the fluctuation in the intensity of the laser light irradiated from the laser medium. Therefore, it is possible to accurately detect particles having a relatively small diameter.

According to another aspect of the present invention, there is provided a light scattering type particle detector comprising a laser medium pumped by pumping laser light, a reflecting mirror on which laser light irradiated from the laser medium is reflected, a flow path defined by sample fluid, and being provided between the laser medium and the reflecting mirror, and a particle detecting region defined by irradiating the laser light to the flow path, the light scattering type particle detector being for detecting particles contained in the particle detecting region by receiving scattered light generated by the laser light, wherein the optical axis of the laser medium and the optical axis of the reflecting mirror are allowed to coincide with each other and a setting angle adjusting means is provided for adjusting setting angles of the laser medium and the reflecting mirror with respect to a setting block for each so as to make the optical axes intersect the flow path.

With this, since setting angles of the laser medium and the reflecting mirror can be adjusted, it is not required to adjust the position of the flow path or a light receiving portion and thereby it is possible to easily adjust the fixation.

According to another aspect of the present invention, in the above-mentioned light scattering type particle detector, the setting angle adjusting means comprises a laser medium setting member to which the laser medium is fixed, the setting angle of which laser medium setting member is adjustable with respect to the setting block for the laser medium, a reflecting mirror setting member to which the reflecting mirror is fixed, the setting angle of which reflecting mirror setting member is adjustable with respect to the setting block for the reflecting mirror, elastic members which are interposed between the laser medium setting member and the setting block for the laser medium and between the reflecting mirror setting member and the setting block for the reflecting mirror.

With this, since the laser medium is fixed to the laser medium setting member, the setting angle of which laser medium setting member is adjustable with respect to the setting block for the laser medium, and the reflecting mirror is fixed to the reflecting mirror setting member, and the setting angle of which reflecting mirror setting member is adjustable with respect to the setting block for the reflecting mirror, it is possible to easily adjust the setting angles of the laser medium and the reflecting mirror.

Further, since elastic members are interposed between the laser medium setting member and the setting block for the laser medium and between the reflecting mirror setting member and the setting block for the reflecting mirror respectively, it is possible to smoothly adjust the setting angles of the laser medium and the reflecting mirror because of the tension between the components created by the elasticity of the elastic members.

According to another aspect of the present invention, in the above-mentioned light scattering type particle detector, the elastic members are O-rings comprised of rubber.

With this, since O-rings comprised of rubber are used, the internal space in which the laser medium and the reflecting mirror are provided is sealed from the outside. As a result of this, air or the like outside of the apparatus cannot enter the internal space and the laser medium or the reflecting mirror is not contaminated.

According to another aspect of the present invention, there is provided a laser oscillator in which pumping laser light generated from a semiconductor laser is condensed to irradiate upon a laser medium with a condenser lens, the laser medium is pumped, and thereby laser light is irradiated, wherein a setting position adjusting means for the semiconductor laser is provided for superposing the intensity distribution (mode) of the pumping laser light generated from the semiconductor laser on the intensity distribution (mode) of the laser light irradiated from the laser medium.

With this, it is possible to make the optical axis of the semiconductor laser coincide with the optical axis of the laser medium. As a result of this, by effectively utilizing the pumping laser light, it is possible to maximize the output.

According to another aspect of the present invention, there is provided a laser oscillator in which pumping laser light generated from a semiconductor laser is condensed to irradiate upon a laser medium with a condenser lens, the laser medium is pumped, and thereby laser light is irradiated, wherein a setting position adjusting means for the condenser lens is provided for superposing the intensity distribution (mode) of the pumping laser light generated from the semiconductor laser on the intensity distribution (mode) of the laser light irradiated from the laser medium.

With this, it is possible to make the condensing position of the pumping laser light coincide with a desired position of the laser medium. As a result of this, by effectively utilizing the pumping laser light, it is possible to maximize the output.

According to another aspect of the present invention, there is provided a laser oscillator in which pumping laser light generated from a semiconductor laser is condensed to irradiate upon a laser medium with a condenser lens, the laser medium is pumped, and thereby laser light is irradiated, wherein a setting position adjusting means for the semiconductor laser and a setting position adjusting means for the condenser lens are provided for superposing the intensity distribution (mode) of the pumping laser light generated from the semiconductor laser on the intensity distribution (mode) of the laser light irradiated from the laser medium.

With this, it is possible to make the optical axis of the semiconductor laser coincide with the optical axis of the laser medium and it is also possible to make the condensing position of the pumping laser light coincide with a desired position of the laser medium. As a result of this, by effectively utilizing the pumping laser light, it is possible to maximize the output.

According to another aspect of the present invention, there is provided a light scattering type particle detector in which the laser light irradiated from the above-mentioned laser oscillator is directed to a flow path defined by sample fluid, and thereby a particle detecting region is defined, particles contained in which particle detecting region are detected by receiving scattered light generated by irradiating the laser light onto said particles.

With this, it is possible to obtain laser light having high output so as to detect fine particles with accuracy.

According to another aspect of the present invention, there is provided a laser oscillator in which pumping laser light generated from a pumping light source is condensed to irradiate upon a solid-state laser with a condenser means and laser light irradiated from the solid-state laser is allowed to irradiate back upon the solid-state laser by a reflecting means, wherein the condenser means has a surface having different radii of curvature in the parallel direction and the perpendicular direction with respect to the flow path.

With this, the pumping laser light generated from the pumping light source is irradiated to the solid-state laser on the condition that the cross section of the pumping laser light is made an elongated shape, and thereby it is possible to make the cross section of the laser light irradiated from the solid-state laser an elongated shape.

According to another aspect of the present invention, there is provided a laser oscillator in which pumping laser light generated from a pumping light source is condensed to irradiate upon a solid-state laser with a condenser means and laser light irradiated from the solid-state laser is allowed to go back to the solid-state laser by a reflecting means, wherein the reflecting means has a surface having different radii of curvature in the parallel direction and the perpendicular direction with respect to the flow path.

With this, the laser light irradiated from the solid-state laser is allowed to go back to the solid-state laser by reflecting from the reflecting means which has a surface having different radii of curvature in the parallel direction and the perpendicular direction with respect to the flow path, and thereby it is possible to make the cross section of the oscillated laser light an elongated shape.

According to another aspect of the present invention, there is provided a laser oscillator in which pumping laser light generated from a pumping light source is condensed to irradiate upon a solid-state laser with a condenser means and laser light irradiated from the solid-state laser is allowed to go back to the solid-state laser by a reflecting means, wherein both of the condenser means and the reflecting means have surfaces having different radii of curvature in the parallel direction and the perpendicular direction with respect to the flow path.

With this, the pumping laser light generated from the pumping light source is irradiated to the solid-state laser on the condition that the cross section of the pumping laser light is made an elongated shape, the laser light irradiated from the solid-state laser is allowed to irradiate back upon the solid-state laser by reflecting from the reflecting means which has a surface having different radii of curvature in the parallel direction and the perpendicular direction with respect to the flow path, and thereby it is possible to make the cross section of the oscillated laser light an elongated shape.

It is also possible thereby to effectively utilize the pumping laser light and increase the intensity of the oscillated laser light.

According to another aspect of the present invention, there is provided a light scattering type particle detector in which the laser light irradiated from the above-mentioned laser oscillator is directed to a flow path defined by sample fluid, and thereby a particle detecting region is defined, particles contained in which particle detecting region are detected by receiving scattered light generated by irradiating the laser light on said particles.

With this, by using laser light having an elongated shape in the transverse mode pattern, it is possible to broaden the particle detecting region without deteriorating the energy density (intensity) of the laser light.

DETAILED DESCRIPTION OF THE PREFERRED EMBODIMENTS

Preferred embodiments of the present invention will now be described with reference to the accompanying drawings.

Figure 1:
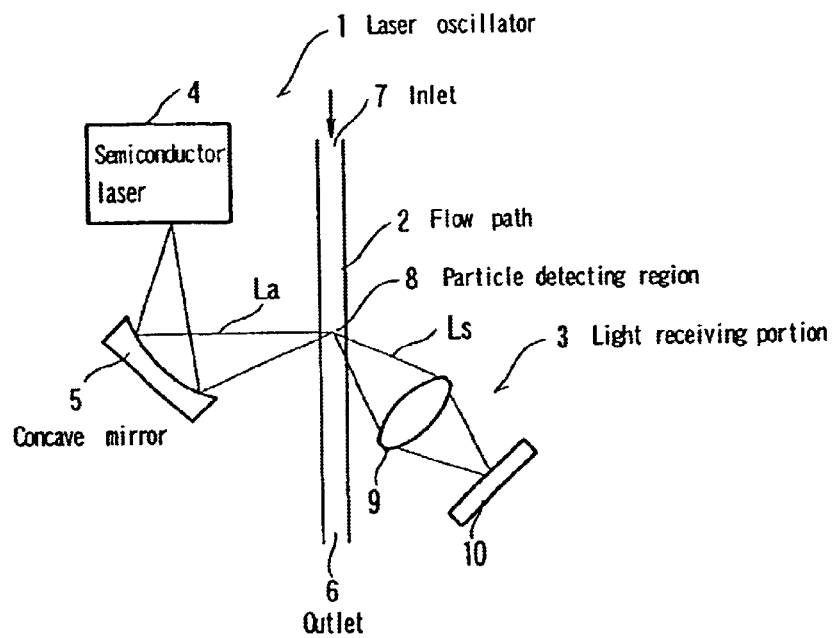
FIG. 1 shows a schematic structure of the first embodiment of a light scattering type particle detector according to the present invention.

The first embodiment of a light scattering type particle detector according to the present invention, as shown in FIG. 1, is comprised of a laser oscillator 1 as a light source, a flow path 2 which is defined by fluid to be detected, and a light receiving portion 3 for receiving scattered light Ls.

The laser oscillator 1 is comprised of a semiconductor laser 4 for generating laser light La and a concave mirror 5 for condensing the laser light La to irradiate upon the flow path 2. Since the semiconductor laser 4 and the concave mirror 5 are not opposed to each other, that is, the optical axis of the semiconductor laser 4 and the optical axis of the concave mirror 5 do not coincide, when the laser light La generated from the semiconductor laser 4 is reflected on the concave mirror 5, the laser light never reflects back to the semiconductor laser 4.

The flow path 2 is defined by fluid to be detected flowing from an inlet 7 to an outlet 6, which fluid is aspirated by an aspirating pump (not shown in the drawing) connected with the downstream portion of the outlet 6. The portion where the laser light La and the flow path 2 intersect is a particle detecting region 8.

The light receiving portion 3 is comprised of a condenser lens 9 for condensing scattered light Ls which is generated at the particle detecting region 8 and a photodiode 10 for photoelectrically converting the scattered light Ls which is condensed. The light receiving portion 3 receives scattered light Ls which is generated by irradiating the laser light La onto particles at the particle detecting region 8 in a case where the fluid contains particles, and outputs electrical signals depending on the intensity of the scattered light Ls.

In the light scattering type particle detector having the above-mentioned structure, it is possible to prevent the laser light La generated from the semiconductor laser 4 from reflecting back to the semiconductor laser 4 and thereby reduce the fluctuation in the intensity of the laser light La generated from the semiconductor laser 4.

Figure 2:
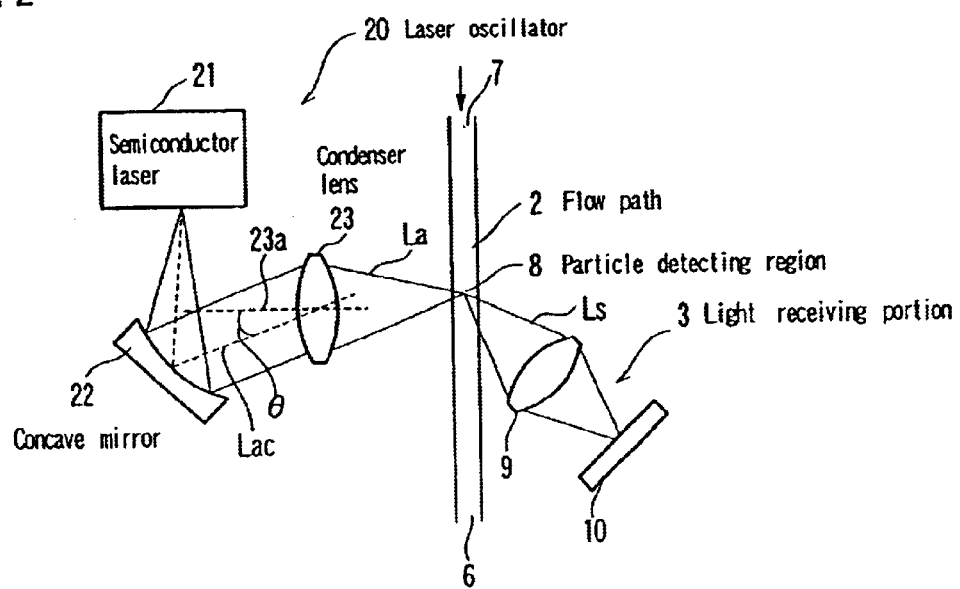
FIG. 2 shows a schematic structure of the second embodiment of a light scattering type particle detector according to the present invention.

The second embodiment of a light scattering type particle detector according to the present invention, as shown in FIG. 2, is comprised of a laser oscillator 20 as a light source, a flow path 2 which is defined by fluid to be detected, and a light receiving portion 3 for receiving scattered light Ls. The explanation of the elements having the same reference number as in FIG. 1 is omitted.

The laser oscillator 20 is comprised of a semiconductor laser 21 for generating laser light La, a concave mirror 22 for deflecting the laser light La by reflection, and a condenser lens 23 for condensing the laser light La which is reflected on the concave mirror 22 into the flow path 2. There is a predetermined angle θ provided between the core axis Lac (chief ray) of the laser light La which is reflected on the concave mirror 22 and the optical axis 23a of the condenser lens 23.

The laser light La which is reflected on the concave mirror 22 is partly reflected on the condenser lens 23 and reflects back to the concave mirror 22. However, since a predetermined angle θ is provided, it is possible to prevent the laser light La which is reflected on the condenser lens 23 from being reflected on the concave mirror 22 again and reflecting back to the semiconductor laser 21.

In the light scattering type particle detector having the above-mentioned structure, by providing a predetermined angle θ between the core axis Lac (chief ray) of the laser light La which is reflected on the concave mirror 22 and the optical axis 23a of the condenser lens 23, it is possible to prevent the laser light La generated from the semiconductor laser 21 from reflecting back to the semiconductor laser 21 and thereby reduce the fluctuation in the intensity of the laser light La generated from the semiconductor laser 21.

Figure 3:
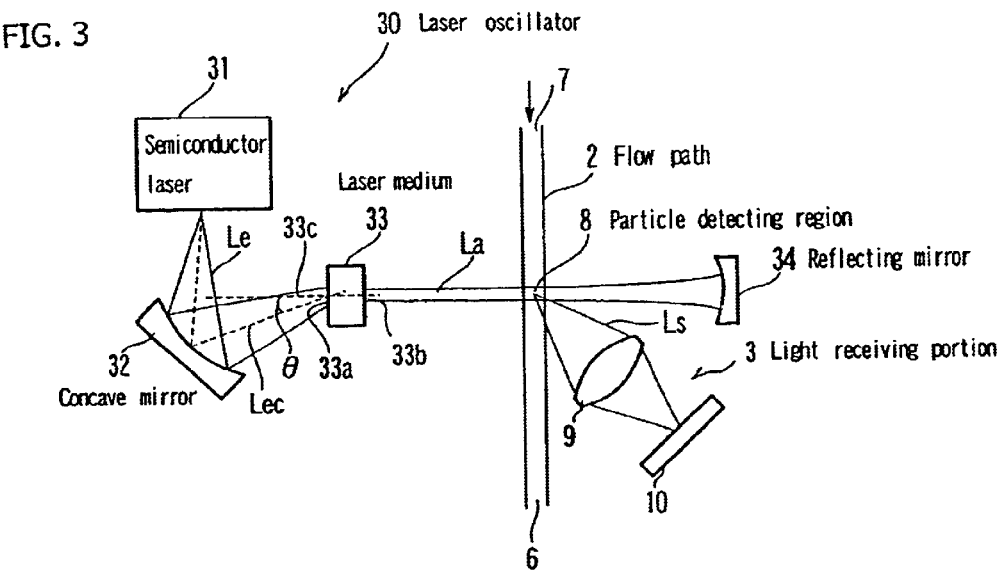
FIG. 3 shows a schematic structure of the third embodiment of a light scattering type particle detector according to the present invention.

The third embodiment of a light scattering type particle detector according to the present invention, as shown in FIG. 3, is comprised of a laser oscillator 30 as a light source, a flow path 2 which is defined by fluid to be detected, and a light receiving portion 3 for receiving scattered light Ls. The explanation of the elements having the same reference number as in FIG. 1 is omitted.

The laser oscillator 30 is comprised of a semiconductor laser 31 for generating pumping laser light Le, a concave mirror 32 for reflecting and condensing the pumping laser light Le, a laser medium 33 which is pumped by the pumping laser light Le condensed with the concave mirror 32 and irradiates laser light La, and a reflecting mirror 34 for reflecting the laser light La irradiated from the laser medium 33. Reflecting mirror 34 is provided to be opposed to the laser medium 33 and the flow path 2 is provided therebetween.

As the laser medium 33, for example, Nd:YVO$_4$, Nd:YAG, or the like can be used. At the end surface 33a of the laser medium 33 facing toward the concave mirror 32 are formed an antireflection coating through which the pumping wavelength of the semiconductor laser 31 (the optical pumping wavelength of the laser medium 33) can penetrate and a reflection coating which reflects the oscillating wavelength of the laser medium 33. At the end surface 33b of the laser medium 33 facing toward the reflecting mirror 34 is formed an antireflection coating that is antireflective with respect to the oscillating wavelength of the laser medium 33.

The laser light La resonates between the laser medium 33 and the reflecting mirror 34. Also, there is a predetermined angle θ provided between the core axis Lec (chief ray) of the pumping laser light Le which is reflected on the concave mirror 32 and the optical axis 33c of the laser medium 33.

The angle θ is determined so as to prevent the pumping laser light Le which is reflected on the end surface 33a of the laser medium 33 or the laser light La which is reflected on the reflecting mirror 34 and transmitted through the end surface 33a from being incident on the light emitting portion of the semiconductor laser 31 as feedback light. Or, even if such light is incident, the angle θ is determined to reduce the incident amount.

In a case where the antireflection coating is applied to the end surface 33a of the laser medium 33 after the angle θ is determined, it is preferable that the antireflection coating is one having properties suitable to be used with the range of the incident angle of the pumping laser light Le which is incident on the end surface 33a so as to prevent the transmission light amount from varying due to the incident angle of the pumping laser light Le.

In a case where the antireflection coating is already applied to the end surface 33a of the laser medium 33, it is preferable that the angle θ is determined depending on the properties of the antireflection coating and taking the range of the incident angle of the pumping laser light Le which is incident on the end surface 33a into consideration so as to prevent the transmission light amount of the pumping laser light Le with respect to the laser medium 33 from being reduced.

The pumping laser light Le which is condensed with the concave mirror 32 is reflected on the laser medium 33 or the laser light La which is irradiated from the laser medium 33 is reflected on the reflecting mirror 34, and thereafter a part of such light is transmitted through the laser medium 33 and goes to the direction of the concave mirror 32. However, since a predetermined angle θ is provided between the core axis Lec (chief ray) of the pumping laser light Le which is reflected on the concave mirror 32 and the optical axis 33c of the laser medium 33, it is possible to prevent the pumping laser light Le or a part of the laser light La from reflecting back to the semiconductor laser 31.

In the light scattering type particle detector having the above-mentioned structure, by providing a predetermined angle θ between the core axis Lec (chief ray) of the pumping laser light Le which is reflected on the concave mirror 32 and the optical axis 33c of the laser medium 33, it is possible to prevent the pumping laser light Le generated from the semiconductor laser 31 from reflecting back to the semiconductor laser 31 or prevent a part of the laser light La from reflecting back to the semiconductor laser 31, and thereby to reduce the fluctuation in the intensity of the pumping laser light Le and the laser light La which is irradiated from the laser medium 33.

Figure 4:
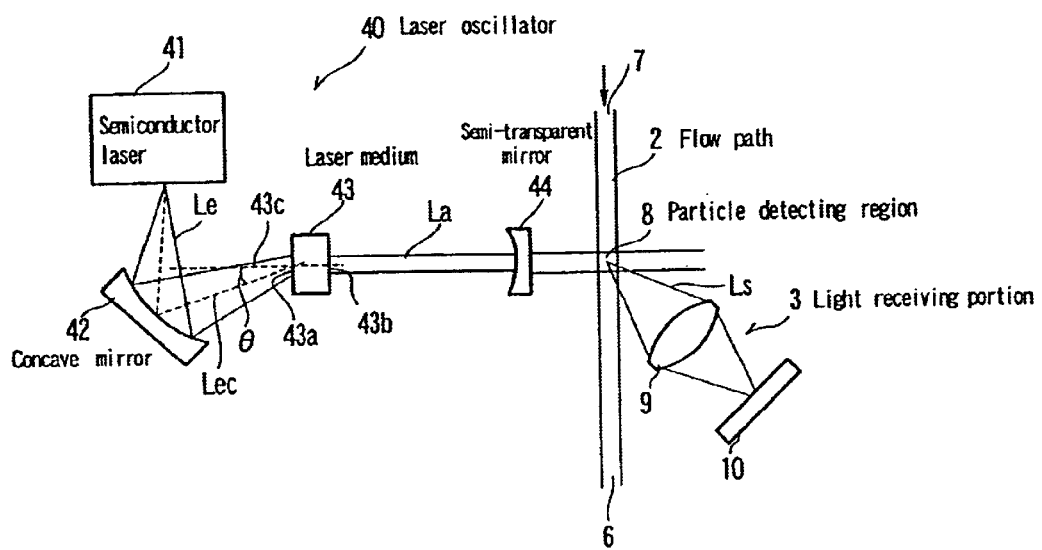
FIG. 4 shows a schematic structure of the fourth embodiment of a light scattering type particle detector according to the present invention.

The fourth embodiment of a light scattering type particle detector according to the present invention, as shown in FIG. 4, is comprised of a laser oscillator 40 as a light source, a flow path 2 which is defined by fluid to be detected, and a light receiving portion 3 for receiving scattered light Ls. The explanation of the elements having the same reference number as in FIG. 1 is omitted.

The laser oscillator 40 is comprised of a semiconductor laser 41 for generating pumping laser light Le, a concave mirror 42 for reflecting and condensing the pumping laser light Le, a laser medium 43 which is pumped by the pumping laser light Le condensed with the concave mirror 42 and irradiates laser light La, and a semi-transparent mirror 44 for reflecting the laser light La irradiated from the laser medium 43, which semi-transparent mirror 44 is provided to be opposed to the laser medium 43.

As the laser medium 43, for example, Nd:YVO$_4$, Nd:YAG, or the like can be used. At the end surface 43a of the laser medium 53 facing toward the concave mirror 42 of the laser medium 43 are formed an antireflection coating through which the pumping wavelength of the semiconductor laser 41 (the optical pumping wavelength of the laser medium 43) can penetrate and a reflection coating which reflects the oscillating wavelength of the laser medium 43. At the end surface 43b of the laser medium 53 facing toward the semi-transparent mirror 44 is formed an antireflection coating that is antireflective with respect to the oscillating wavelength of the laser medium 43.

The laser light La resonates between the laser medium 43 and the semi-transparent mirror 44 and a part of the laser light La is transmitted through the semi-transparent mirror 44 and irradiates a particle detecting region 8. Also, there is a predetermined angle θ provided between the core axis Lec (chief ray) of the pumping laser light Le which is reflected on the concave mirror 42 and the optical axis 43c of the laser medium 43.

The angle θ is determined so as to prevent the pumping laser light Le which is reflected on the end surface 43a of the laser medium 43 or the laser light La which is reflected on the semi-transparent mirror 44 and transmitted through the end surface 43a from being incident on the light emitting portion of the semiconductor laser 41 as feedback light. Or, even if such light is incident, the angle θ is determined to reduce the incident amount.

In a case where the antireflection coating is applied to the end surface 43a of the laser medium 43 after the angle θ is determined, it is preferable that the antireflection coating is one having properties suitable to be used with the range of the incident angle of the pumping laser light Le which is incident on the end surface 43a so as to prevent the transmission light amount from varying due to the incident angle of the pumping laser light Le.

In a case where the antireflection coating is already applied to the end surface 43a of the laser medium 43, it is preferable that the angle θ is determined depending on the properties of the antireflection coating and taking the range of the incident angle of the pumping laser light Le which is incident on the end surface 43a into consideration so as to prevent the transmission light amount of the pumping laser light Le with respect to the laser medium 43 from being reduced.

The pumping laser light Le which is condensed with the concave mirror 42 is reflected on the laser medium 43 or the laser light La which is irradiated from the laser medium 43 is reflected on the semi-transparent mirror 44, and thereafter a part of such light is transmitted through the laser medium 43 and goes to the side of the concave mirror 42. However, since a predetermined angle θ is provided between the core axis Lec (chief ray) of the pumping laser light Le which is reflected on the concave mirror 42 and the optical axis 43c of the laser medium 43, it is possible to prevent the pumping laser light Le or a part of the laser light La from reflecting back to the semiconductor laser 41.

In the light scattering type particle detector having the above-mentioned structure, by providing a predetermined angle θ between the core axis Lec (chief ray) of the pumping laser light Le which is reflected on the concave mirror 42 and the optical axis 43c of the laser medium 43, it is possible to prevent the pumping laser light Le generated from the semiconductor laser 41 from reflecting back to the semiconductor laser 41 or prevent a part of the laser light La from reflecting back to the semiconductor laser 41, and thereby to reduce the fluctuation in the intensity of the pumping laser light Le and the laser light La which is irradiated from the laser medium 43.

A concave mirror refers to a reflecting mirror curved in a concave shape. For example, a spherical concave mirror may be used in the present invention. In addition, by using an aspherical concave mirror, it is possible to increase the condensing efficiency and thereby irradiate laser light La having a high energy density and a desired intensity pattern to the particle detecting region 8.

The fifth embodiment of a light scattering type particle detector according to the present invention, as shown in FIG.

5, is comprised of a laser oscillator 50 as a light source, a flow path 2 which is defined by fluid to be detected, and a light receiving portion 3 for receiving scattered light Ls.

The laser oscillator 50 is comprised of a semiconductor laser 51 for generating pumping laser light Le, a condenser lens 52 for reflecting and condensing the pumping laser light Le, a laser medium 53 which is pumped by the pumping laser light Le condensed with the condenser lens 52 and irradiates laser light La, and a reflecting mirror 54 for reflecting the laser light La which is irradiated from the laser medium 53, which reflecting mirror 54 is provided to be opposed to the laser medium 53 in which the flow path 2 is provided therebetween. As shown, the semiconductor laser 51 is disposed at a nonlinear angle to the optical axis of the laser medium 53.

As the laser medium 53, for example, Nd:YVO$_4$, Nd:YAG, or the like can be used. At the end surface 53a of the laser medium 53 facing toward the condenser lens 52 are formed an antireflection coating through which the pumping wavelength of the semiconductor laser 51 (the optical pumping wavelength of the laser medium 53) can penetrate and a reflection coating which reflects the oscillating wavelength of the laser medium 53. At the end surface 53b of the laser medium 53 facing toward the reflecting mirror 54 is formed an antireflection coating that is antireflective with respect to the oscillating wavelength of the laser medium 53.

There is a predetermined angle θ provided between the optical axis 51a of the semiconductor laser 51 and the optical axis 53c of the laser medium 53.

The angle θ is determined so as to prevent the pumping laser light Le which is reflected on the end surface 53a of the laser medium 53 or the laser light La which is reflected on the reflecting mirror 54 and transmitted through the end surface 53a from being incident on the light emitting portion of the semiconductor laser 51 as feedback light. Or, even if such light is incident, the angle θ is determined to reduce the incident amount.

In a case where the antireflection coating is applied to the end surface 53a of the laser medium 53 after the angle θ is determined, it is preferable that the antireflection coating is one having properties suitable to be used with the range of the incident angle of the pumping laser light Le which is incident on the end surface 53a so as to prevent the transmission light amount from varying due to the incident angle of the pumping laser light Le.

In a case where the antireflection coating is already applied to the end surface 53a of the laser medium 53, it is preferable that the angle θ is determined depending on the properties of the antireflection coating and taking the range of the incident angle of the pumping laser light Le which is incident on the end surface 53a into consideration so as to prevent the transmission light amount of the pumping laser light Le with respect to the laser medium 53 from being reduced.

In addition, it is also necessary that the determination of the angle θ should be varied depending on the magnitude of the condensing half-angle of the condenser lens 52. As the properties of the semiconductor laser 51, the divergence angle of the beam thereof is large (for example, around 30°). Therefore, it becomes necessary to determine the angle θ taking the condensing half-angle of the condenser lens 52 into consideration so as to prevent the transmission light amount of the pumping laser light Le with respect to the laser medium 53 from being reduced.

For example, if a condenser lens having a condensing half-angle of 40° is used as the condenser lens 52, it is preferable to set the angle θ within 30°. With this, it is possible to maintain the transmission light amount of the pumping laser light Le with respect to the laser medium 53 at a desired level and also to reduce feedback light from the end surface 53a of the laser medium 53.

As mentioned above, the angle θ provided between the optical axis 51a of the semiconductor laser 51 and the optical axis 53c of the laser medium 53 is determined depending on the properties of the antireflection coating which is applied to the end surface 53a of the laser medium 53, the range of the incident angle of the pumping laser light Le which is incident on the end surface 53a of the laser medium 53, and the condensing half-angle of the condenser lens 52.

The flow path 2 is defined by fluid to be detected flowing from an inlet 7 to an outlet 6, which fluid is aspirated by an aspirating pump (not shown in the drawing) connected with the downstream portion of the outlet 6. The portion where the laser light La and the flow path 2 intersect is a particle detecting region 8.

The light receiving portion 3 is comprised of a condenser lens 9 for condensing scattered light Ls which is generated at the particle detecting region 8 and a photodiode 10 for photoelectrically converting the scattered light Ls which is condensed. The light receiving portion 3 receives scattered light Ls which is generated by irradiating the laser light La onto particles at the particle detecting region 8 in a case where the fluid contains particles, and outputs electrical signals depending on the intensity of the scattered light Ls.

The operation of the fifth embodiment of a light scattering type particle detector according to the present invention having the above-mentioned structure will be described hereinafter.

Pumping laser light Le generated from the semiconductor laser 51 is condensed to irradiate upon the end surface 53a of the laser medium 53 with the condenser lens 52. Even if the pumping laser light Le is reflected on the end surface 53a of the laser medium 53, by providing the angle θ between the optical axis 51a of the semiconductor laser 51 and the optical axis 53c of the laser medium 53 the pumping laser light Le is prevented from going back to the semiconductor laser 51.

Also, the laser medium 53 is pumped by the pumping laser light Le and laser light La is irradiated therefrom. The laser light La is reflected on the reflecting mirror 54, a part of the reflected light is transmitted through the laser medium 53 and is incident to the direction of the condenser lens 52. However, by providing the angle θ between the optical axis 51a of the semiconductor laser 51 and the optical axis 53c of the laser medium 53, the part of the laser light La is prevented from reflecting back to the light emitting portion of the semiconductor laser 51.

Therefore, by applying an antireflection coating through which the pumping wavelength of the semiconductor laser 51 can penetrate and a reflection coating which reflects the oscillating wavelength of the laser medium 53 to the end surface 53a of the laser medium 53, and also by providing the angle θ between the optical axis 51a of the semiconductor laser 51 and the optical axis 53c of the laser medium 53, it is possible to prevent the pumping laser light Le generated from the semiconductor laser 51 from reflecting back to the light emitting portion of the semiconductor laser 51 or to prevent a part of the laser light La from going back to the light emitting portion of the semiconductor laser 51 as much as possible, and thereby to reduce the fluctuation in the intensity of the pumping laser light Le and the laser light La irradiated from the laser medium 53.

The light receiving portion 3 receives scattered light Ls which is generated by irradiating the laser light La onto particles at the particle detecting region 8, and outputs electrical signals depending on the intensity of the scattered light Ls. It is possible to recognize the presence of particles and the particle diameter thereof through the level of the electrical signals outputted by the light receiving portion 3. Since deterioration of the signal-to-noise ratio in the particle detection is avoided by reducing the fluctuation in the intensity of the laser light La, it is possible to accurately detect particles having a relatively small diameter.

Figure 5:
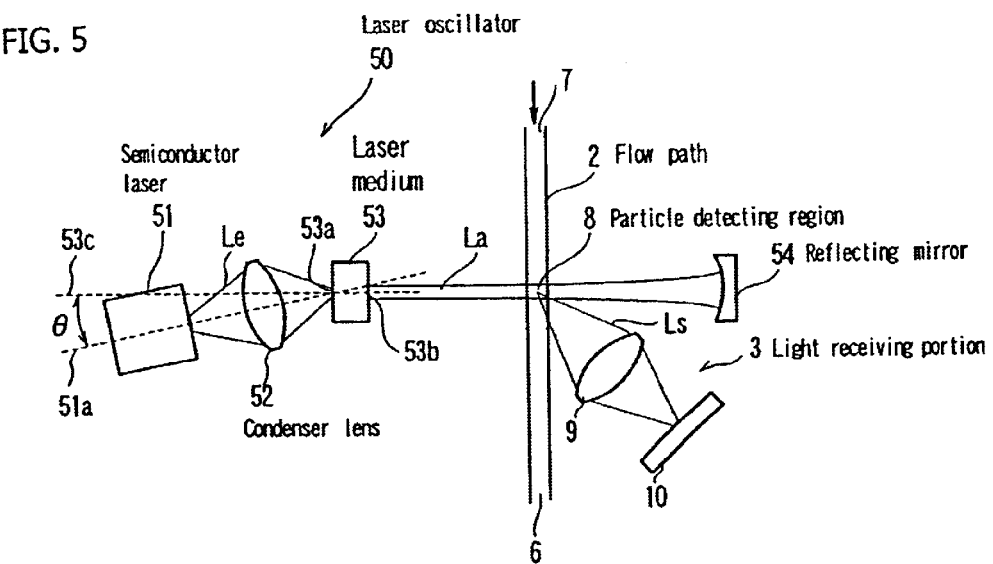
FIG. 5 shows a schematic structure of the fifth embodiment of a light scattering type particle detector according to the present invention.
Figure 6:
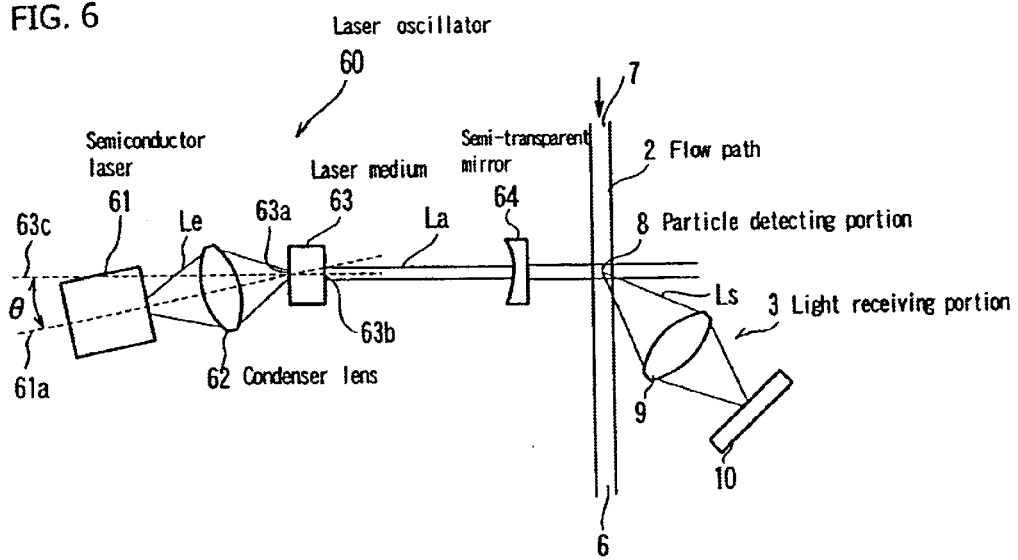
FIG. 6 shows a schematic structure of the sixth embodiment of a light scattering type particle detector according to the present invention.

In the sixth embodiment of a light scattering type particle detector according to the present invention, as shown in FIG. 6, a flow path 2 which is defined by fluid to be detected is provided not within the resonating region of the laser light La but outside of a laser oscillator 60. In this case, the portion where the laser light La which is irradiated to the outside of the laser oscillator 60 and the flow path 2 intersect may be a particle detecting region 8. However, it is necessary to use a semi-transparent mirror 64 instead of the reflecting mirror 54 shown in FIG. 5.

Therefore, the laser oscillator 60 is comprised of a semiconductor laser 61 for generating pumping laser light Le, a condenser lens 62 for condensing the pumping laser light Le, a laser medium 63 which is pumped by the pumping laser light Le condensed with the condenser lens 62 and thereupon emits laser light La, and a semi-transparent mirror 64 for reflecting the laser light La irradiated from the laser medium 63, which semi-transparent mirror 64 is provided to be opposed to the laser medium 63.

As the laser medium 63, for example, Nd:YVO$_4$, Nd:YAG, or the like can be used. At the end surface 63a of the laser medium 63 facing toward the condenser lens 62 are formed an antireflection coating through which the pumping wavelength of the semiconductor laser 61 (the optical pumping wavelength of the laser medium 63) can penetrate and a reflection coating which reflects the oscillating wavelength of the laser medium 63. At the end surface 63b of the laser medium 63 facing toward the semi-transparent mirror 64 is formed an antireflection coating that is antireflective with respect to the oscillating wavelength of the laser medium 63.

There is a predetermined angle θ provided between the optical axis 61a of the semiconductor laser 61 and the optical axis 63c of the laser medium 63.

The angle θ is determined so as to prevent the pumping laser light Le which is reflected on the end surface 63a of the laser medium 63 or the laser light La which is reflected on the semi-transparent mirror 64 and transmitted through the end surface 63a from being incident on the light emitting portion of the semiconductor laser 61 as feedback light. Or, even if such light is incident, the angle θ is determined to reduce the incident amount.

In a case where the antireflection coating is applied to the end surface 63a of the laser medium 63 after the angle θ is determined, it is preferable that the antireflection coating is one having properties suitable to be used with the range of the incident angle of the pumping laser light Le which is incident on the end surface 63a so as to prevent the transmission light amount from varying due to the incident angle of the pumping laser light Le.

In a case where the antireflection coating is already applied to the end surface 63a of the laser medium 63, it is preferable that the angle θ is determined depending on the properties of the antireflection coating and taking the range of the incident angle of the pumping laser light Le which is incident on the end surface 63a into consideration so as to prevent the transmission light amount of the pumping laser light Le with respect to the laser medium 63 from being reduced.

The laser light La resonates between the laser medium 63 and the semi-transparent mirror 64. A part of the laser light La is transmitted through the semi-transparent mirror 64 and thereby irradiates a particle detecting region 8. An explanation of the elements having the same reference number as in FIG. 5 is omitted.

The operation of the sixth embodiment of a light scattering type particle detector according to the present invention is same as that of the light scattering type particle detector shown in FIG. 5. Therefore, an explanation is omitted.

In the light scattering type particle detector shown in FIG. 6, by providing a flow cell made of a transparent material between an inlet 7 and an outlet 6 of a flow path 2, it is possible to pass liquid therethrough and thereby particles contained in liquid can be detected.

Figure 7:
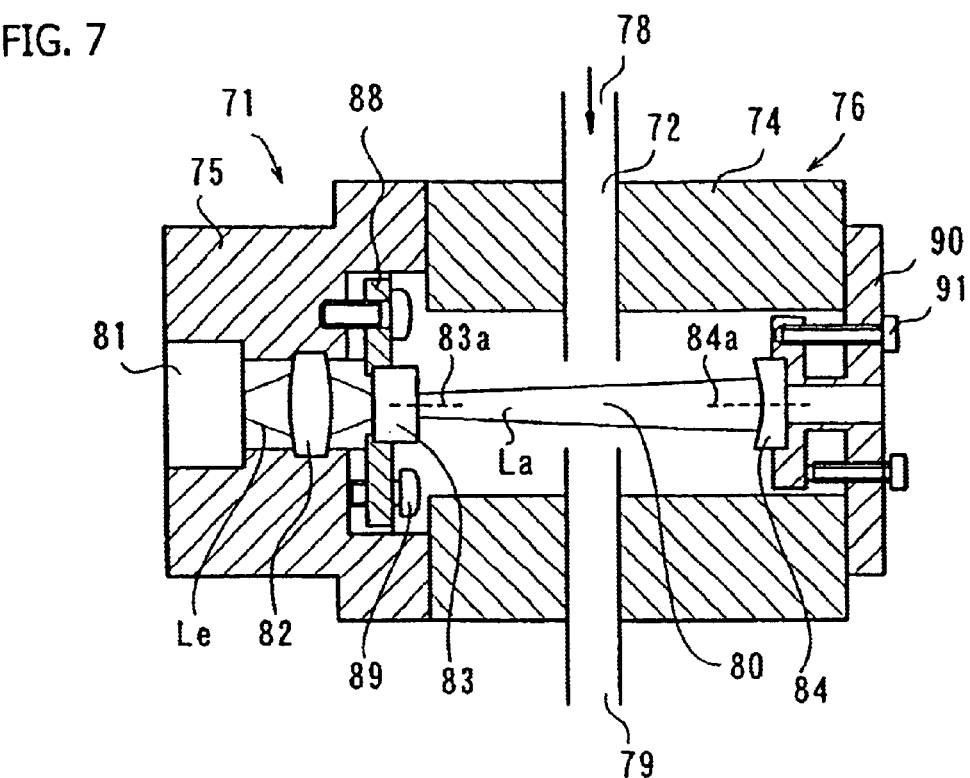
FIG. 7 is a cross-sectional view showing schematic structure of the seventh embodiment of a light scattering type particle detector according to the present invention.
Figure 8:
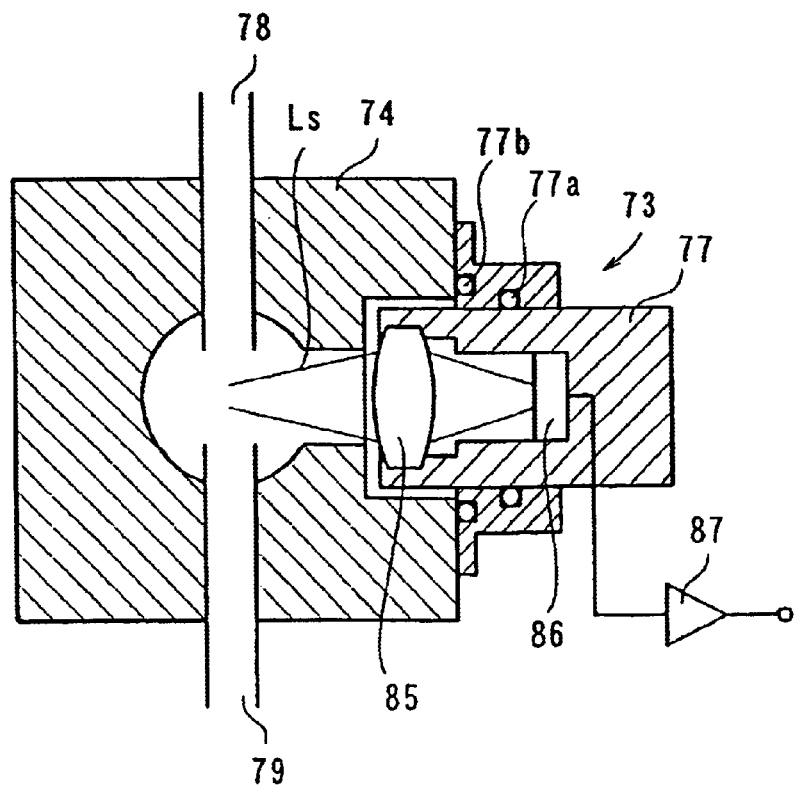
FIG. 8 is a cross-sectional view showing a schematic diagram of a light receiving portion.

The seventh embodiment of a light scattering type particle detector according to the present invention, as shown in FIGS. 7 and 8, is comprised of a laser oscillator 71 as a light source, a flow path 72 which is defined by fluid to be detected, and a light receiving portion 73 for receiving scattered light Ls. The laser oscillator 71 is housed within a case 76 which is comprised of a first setting block 74 and a second setting block 75, both blocks being hollow. The light receiving portion 73 is housed within a light receiving case 77 which is fixed to the side surface of the first setting block 74.

The laser oscillator 71 is comprised of a semiconductor laser 81 for generating pumping laser light Le, a condenser lens 82 for condensing the pumping laser light Le, a laser medium 83 which is pumped by the pumping laser light Le condensed with the condenser lens 82 and thereupon emits laser light La, and a reflecting mirror 84 for reflecting the laser light La which is irradiated from the laser medium 83 and allowing the reflected light to go back to the laser medium 83, which reflecting mirror 84 is provided to be opposed to the laser medium 83 in which the flow path 72 is provided therebetween.

As the laser medium 83, for example, Nd:YVO$_4$, Nd:YAG, or the like can be used. At the end surface of the laser medium 83 facing toward the condenser lens 82 are formed an antireflection coating through which the pumping wavelength of the semiconductor laser 81 (the optical pumping wavelength of the laser medium 83) can penetrate and a reflection coating which reflects the oscillating wavelength of the laser medium 83. At the end surface of the laser medium 83 facing toward the reflecting mirror 84 of the laser medium 83 is formed an antireflection coating that is antireflective with respect to the oscillating wavelength of the laser medium 83. The laser light La resonating between the laser medium 83 and the reflecting mirror 84 is perpendicular to the end surface of the laser medium 83.

The flow path 72 is defined by fluid to be detected flowing between an inlet 78 and an outlet 79 which are provided in the first setting block 74. The inlet 78 and the outlet 79 are provided so that the flow path 72 orthogonally intersects or otherwise intersects the core axis of the first setting block 74. The fluid is aspirated by an aspirating pump (not shown in the drawing) connected with the downstream portion of the outlet 79 and thereby flows from the inlet 78 to the outlet 79. The portion where the laser light La and the flow path 72 intersect is a particle detecting region 80.

The light receiving portion 73 is comprised of a condenser lens 85 for condensing scattered light Ls which is generated at the particle detecting region 80, a photodiode 86 for photoelectrically converting the condensed scattered light Ls, and an amplifier 87. The light receiving portion 73 receives scattered light Ls which is generated by irradiating the laser light La onto particles at the particle detecting region 80 in a case where the fluid contains particles, and outputs electrical signals depending on the intensity of the scattered light Ls. The reference numbers 77a and 77b refer to O-rings.

As shown in FIG. 7, the laser medium 83 is attached to the second setting block 75 through a laser medium setting member 88 having a disk form. The irradiation port of the laser medium 83 which is on the optical axis 83a (the irradiation direction of the laser light La) of the laser medium 83 is arranged to be on the core axis of the laser medium setting member 88. Also, the core axis of the laser medium setting member 88 and the core axis of the second setting block 75 are arranged to coincide with each other.

Figure 9:
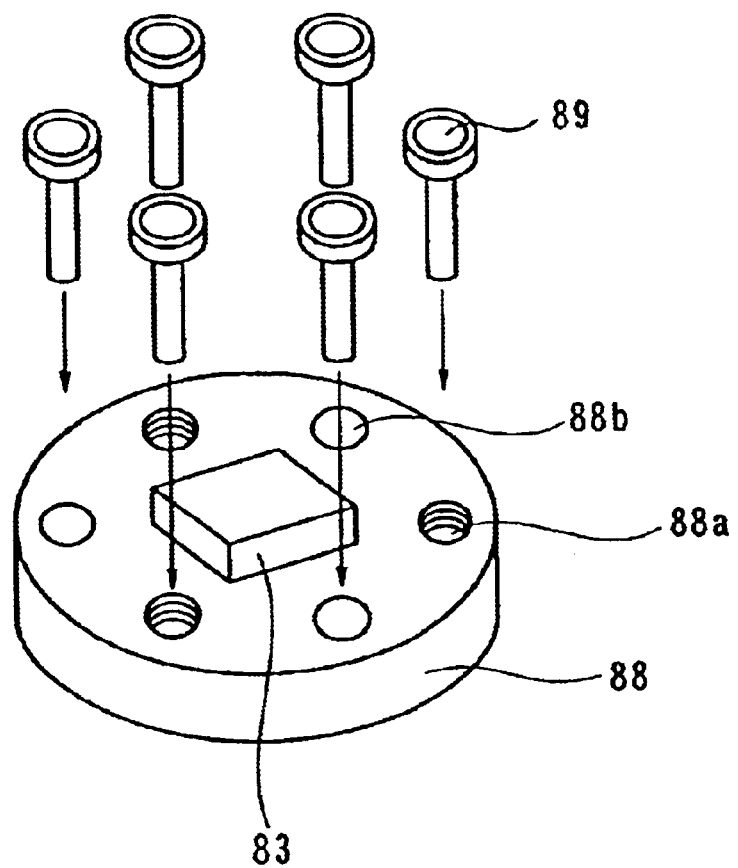
FIG. 9 is a perspective view of a laser medium setting member.

The laser medium setting member 88 has a penetrating hole for passing the pumping laser light Le generated from the semiconductor laser 81 therethrough in the center portion. As shown in FIG. 9, the laser medium setting member 88 has also holes 88a in which a thread is formed and holes 88b in which a thread is not formed. The holes 88a and the holes 88b are alternately formed in the edge portion of the 6-sected circle of the laser medium setting member 88.

A bolt 89 is twisted into each of the three holes 88a, and the top portion of the bolt 89 abuts against the surface of the second setting block 75 as shown in FIG. 7. A bolt 89 is inserted through each of the three holes 88b, and the top portion of the bolt 89 is twisted into a threaded hole which is formed in the second setting block 75.

Therefore, by adjusting the amount of insertion of the three bolts 89 into the three holes 88a and the amount of insertion of the three bolts 89 inserted through the three holes 88b into the second setting block 75, it is possible to attach the laser medium setting member 88 in an inclined condition as desired with respect to the second setting block 75. With this, it is also possible to make the laser medium 83 which is attached to the laser medium setting member 88 inclined with respect to the second setting block 75.

As shown in FIG. 7, the reflecting mirror 84 is attached to the first setting block 74 through a reflecting mirror setting member 90. The center of the reflecting surface which is on the optical axis 84a (the irradiation direction of the laser light La) of the reflecting mirror 84 is arranged to be on the core axis of the reflecting mirror setting member 90. Also, the core axis of the reflecting mirror setting member 90 and the core axis of the first setting block 74 are arranged to coincide with each other.

Figure 10:
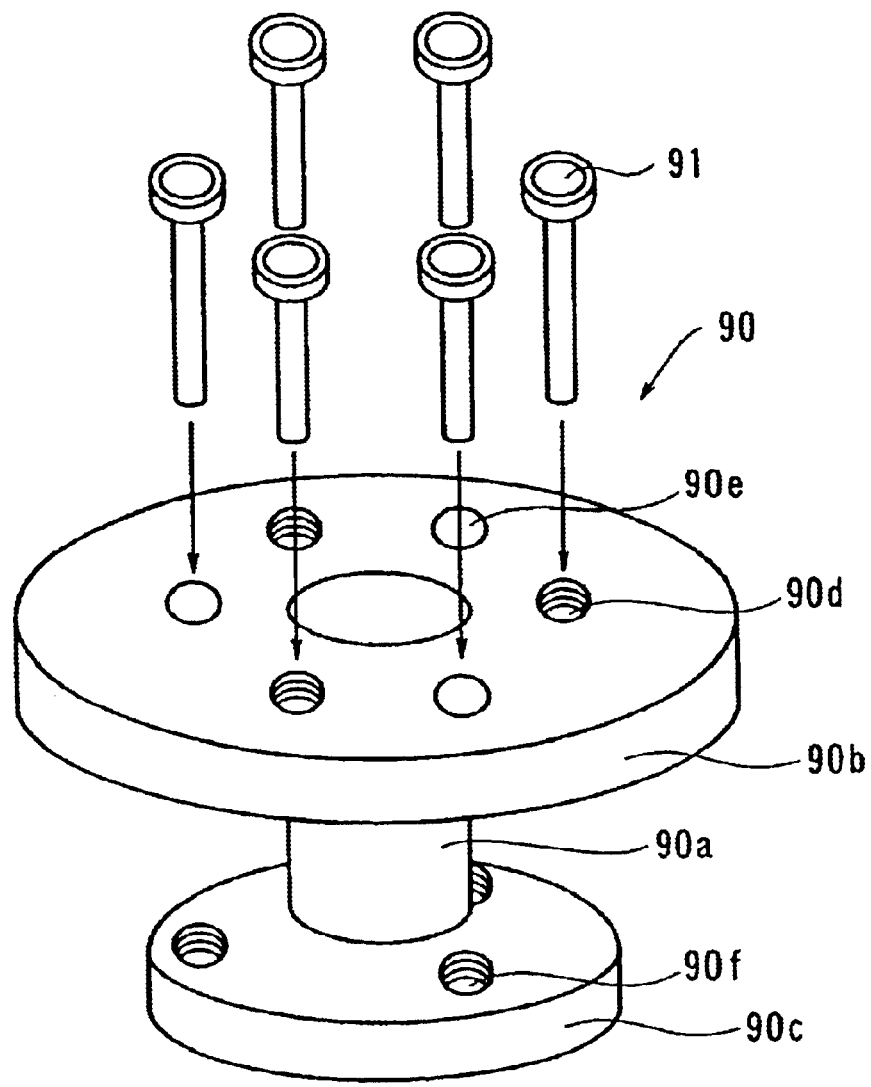
FIG. 10 is a perspective view of a reflecting mirror setting member.

As shown in FIG. 10, the reflecting mirror setting member 90 is comprised of a thin cylinder member 90a with a flange 90b having a large diameter and a flange 90c having a small diameter integrally formed at opposing ends thereof. The flange 90b having a large diameter has holes 90d in which a thread is formed and holes 90e in which a thread is not formed. The holes 90d and the holes 90e are alternately formed in the edge portion of the 6-sectioned circle of the flange 90b having a large diameter.

A bolt 91 is twisted into each of the three holes 90d, and the top portion of the bolt 91 abuts against the surface of the flange 90c having a small diameter as shown in FIG. 7. A bolt 91 is inserted through each of the three holes 90e, and the top portion of the bolt 91 is twisted into the threaded hole 90f which is formed in the flange 90c having a small diameter.

Therefore, by adjusting the amount of insertion of the three bolts 91 into the three holes 90d and the amount of insertion of the three bolts 91 inserted through the three holes 90e into the three threaded holes 90f of the flange 90c, so as to make the thin cylinder member 90a bend, it is possible to attach the reflecting mirror setting member 90 in an inclined condition as desired with respect to the first setting block 74. With this, it is also possible to make the reflecting mirror 84 which is attached to the reflecting mirror setting member 90 inclined with respect to the first setting block 74.

The fixation adjustment in the seventh embodiment of a light scattering type particle detector according to the present invention having the above-mentioned structure will be described hereinafter.

Figure 11:
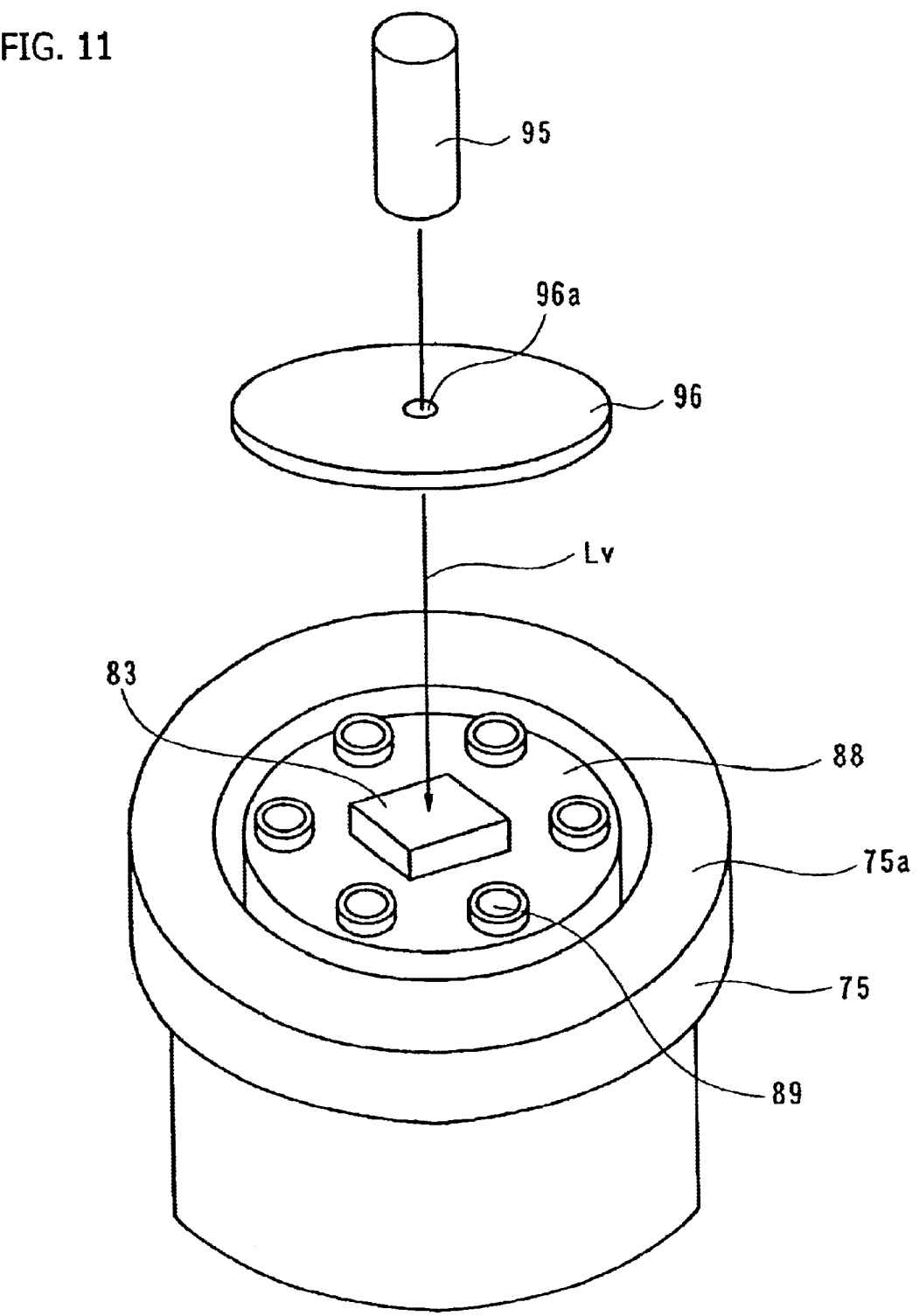
FIG. 11 is a view for explaining the adjustment in the setting angle of the laser medium setting member.

First, the setting angle of the laser medium 83 is adjusted with respect to the second setting block 75. This adjustment is conducted with a laser light source 95 for generating adjustment laser light Lv and a shutter plate 96 for passing the laser light Lv therethrough, as shown in FIG. 11.

The laser medium 83 is attached to the second setting block 75 through the laser medium setting member 88 and the laser light source 95 and the shutter plate 96 are set to a setting angle adjustment jig (not shown in the drawing). In this instance, a surface 75a of the second setting block 75 is perpendicular to the irradiation direction of the laser light Lv and the core axis of the second setting block 75 coincides with the irradiation direction of the laser light Lv. In addition, the shutter plate 96 is set so that the laser light Lv passes a hole 96a which is formed in the shutter plate 96.

Next, laser light Lv is generated from the laser light source 95. The setting angle of the laser medium setting member 88 is adjusted with respect to the second setting block 75 by twisting the six bolts 89 alternately, so that light reflected on the end surface of the laser medium 83 can pass the hole 96a of the shutter plate 96.

When the reflected light passes through the hole 96a of the shutter plate 96, the laser medium 83 is perpendicular to the surface 75a of the second setting block 75 and irradiates the laser light La in the direction corresponding to the core axis of the second setting block 75.

Therefore, the adjustment is thereby finished because the purpose of adjusting the setting angle of the laser medium 83 with respect to the second setting block 75 is to make the optical axis 83a (the irradiation direction of the laser light La) of the laser medium 83 and the core axis of the second setting block 75 coincide with each other.

Next, the first setting block 74 to which the reflecting mirror 84 is set through the reflecting mirror setting member 90 is fixed to the second setting block 75 to which the laser medium 83 is set wherein the above-mentioned adjustment of the setting angle is finished. With this, the assembly of the light scattering type particle detector is finished. In this instance, the core axis of the first setting block 74 and the core axis of the second setting block 75 coincide with each other.

Next, the setting angle of the reflecting mirror 84 is adjusted with respect to the first setting block 74. This adjustment is conducted by twisting the six bolts 91 alternately so as to maximize the output voltage of the light receiving portion 73 which is dependent on the scattered light Ls generated by standard particles contained in air flowing through the flow path 72 in the assembled light scattering type particle detector.

Also, this adjustment may be conducted by twisting the six bolts 91 alternately so as to maximize the transmission light amount in the reflecting mirror 84 which is monitored using an optical power meter.

When the voltage depending on the scattered light Ls is maximized, the laser oscillation is most effectively conducted, and the irradiation direction of the laser light La irradiated from the laser medium 83, that is, the optical axis 83a of the laser medium 83 coincides with the optical axis 84a of the reflecting mirror 84.

The adjustment is finished with this step having satisfied the purpose of adjusting the setting angle of the reflecting mirror 84 with respect to the first setting block 74 to make the optical axis 84a (the irradiation direction of the laser light La) of the reflecting mirror 84 and the core axis of the first setting block 74 coincide with each other.

Figure 12:
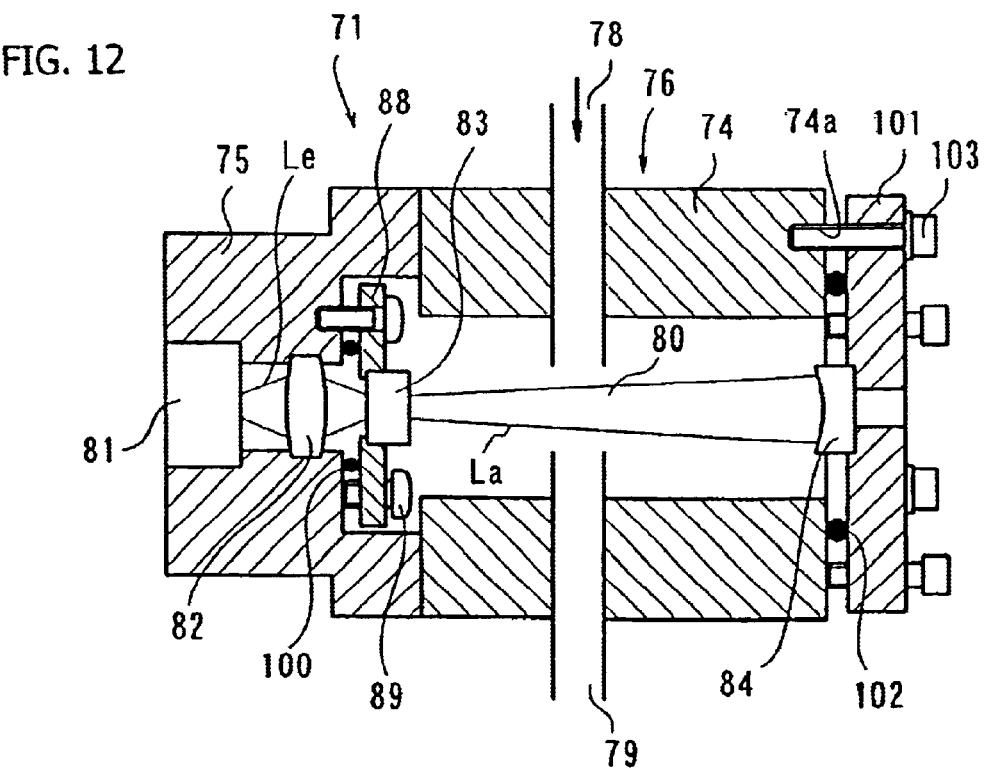
FIG. 12 is a cross-sectional view showing a schematic structure of the eighth embodiment of a light scattering type particle detector according to the present invention.

The eighth embodiment of a light scattering type particle detector according to the present invention shown in FIG. 12 is different from the above-mentioned light scattering type particle detector shown in FIG. 7, in that an O-ring 100 made of rubber is provided between the laser medium setting member 88 and the second setting block 75, a reflecting mirror setting member 101 has a different shape from that of the reflecting mirror setting member 90, three threaded holes 74a are formed at the end portion of the first setting block 74, the reflecting mirror setting member 101 is fixed with the threaded holes 74a or the like, an O-ring 102 made of rubber is provided between the reflecting mirror setting member 101 and the first setting block 74. An explanation of the elements in FIG. 12 having the same reference number as in FIG. 7 is omitted.

The O-ring 100 interposed between the laser medium setting member 88 and the second setting block 75 functions to separate the laser medium setting member 88 and the second setting block 75 with its elasticity. This makes it possible to smoothly conduct the adjustment of the setting angle of the laser medium setting member 88 with respect to the second setting block 75 which is conducted by adjusting the insertion amount of the six bolts 89.

Figure 13:
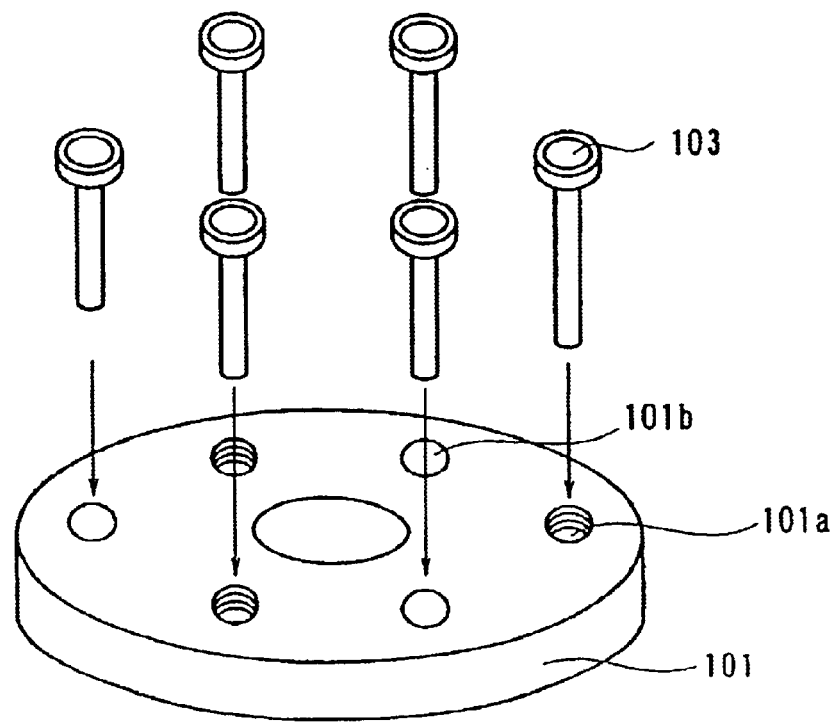
FIG. 13 is a perspective view of a reflecting mirror setting member of the eighth embodiment of a light scattering type particle detector according to the present invention.

The reflecting mirror 84 is set to the center of the reflecting mirror setting member 101 having a disk form. As shown in FIG. 13, the reflecting mirror setting member 101 has holes 101a in which a thread is formed and holes 101b in which a thread is not formed. The holes 101a and the holes 101b are alternately formed in the edge portion of the 6-sectioned circle of the reflecting mirror setting member 101.

A bolt 103 is twisted into each of the three holes 101a, and the top portion of the bolt 103 abuts against the surface of the first setting block 74 as shown in FIG. 12. A bolt 103 is inserted through each of the three holes 101b, and the top (threaded end) portion of the bolt 103 is twisted into each of the three threaded holes 74a which are formed in the first setting block 74.

Therefore, by adjusting the amount of insertion of the three bolts 103 into the three holes 101a and the amount of insertion of the three bolts 103 inserted through the three holes 101b into the first setting block 74, it is possible to attach the reflecting mirror setting member 101 in an inclined condition as desired with respect to the first setting block 74. This also makes it possible to make the reflecting mirror 84 attached to the reflecting mirror setting member 101 inclined with respect to the first setting block 74.

In this instance, the O-ring 102 interposed between the reflecting mirror setting member 101 and the first setting block 74 functions to separate the reflecting mirror setting member 101 and the first setting block 74 with its elasticity. This makes it possible to smoothly conduct the adjustment of the setting angle of the reflecting mirror setting member 101 with respect to the first setting block 74 which is conducted by adjusting the insertion of the six bolts 103.

In addition, in the light scattering type particle detector shown in FIG. 12, since the O-ring 100 is interposed between the laser medium setting member 88 and the second setting block 75 and the O-ring 102 is interposed between the reflecting mirror setting member 101 and the first setting block 74, the internal space of the case 76 is sealed from the outside by providing a seal between the first setting block 74 and the second setting block 75. As a result of this, air or the like outside of the assembly cannot enter the internal space of the case 76 and therefore the optical devices such as the laser medium 83 and the reflecting mirror 84 which are positioned within the case 76 are not contaminated.

Figure 14:
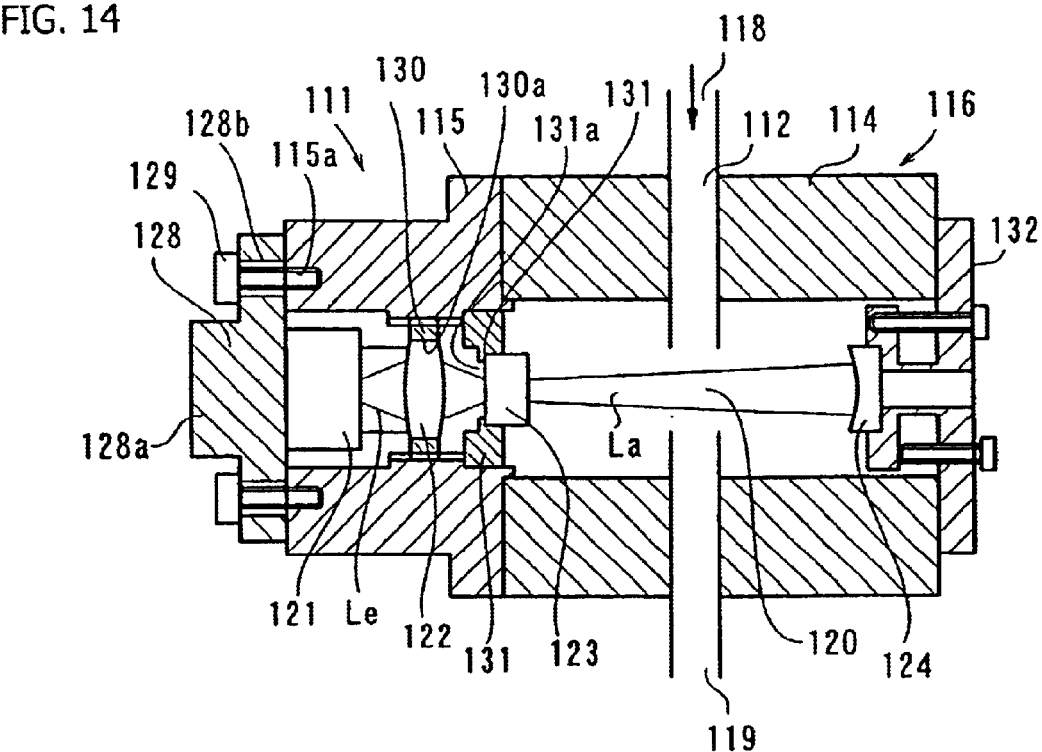
FIG. 14 is a cross-sectional view showing a schematic structure of the ninth embodiment of a light scattering type particle detector according to the present invention.

The ninth embodiment of a light scattering type particle detector according to the present invention, as shown in FIG. 14, is comprised of a laser oscillator 111 as a light source, a flow path 112 which is defined by fluid to be detected, and a light receiving portion for receiving scattered light Ls (not shown in the drawing). The laser oscillator 111 is housed within a case 116 comprised of a first setting block 114 and a second setting block 115, both blocks being hollow. The light receiving portion is housed within a light receiving case which is fixed to the side surface of the first setting block 114.

The laser oscillator 111 is comprised of a semiconductor laser 121 for generating pumping laser light Le, a condenser lens 122 for condensing the pumping laser light Le, a laser medium 123 which is pumped by the pumping laser light Le condensed with the condenser lens 122 and irradiates laser light La, and a reflecting mirror 124 for reflecting the laser light La which is emitted from the laser medium 123 and allowing the reflected light to go back to the laser medium 123, which reflecting mirror 124 is provided to be opposed to the laser medium 123 in which the flow path 112 is provided therebetween.

The flow path 112 is defined by fluid to be detected flowing between an inlet 118 and an outlet 119 which are provided in the first setting block 114. The inlet 118 and the outlet 119 are provided so that the flow path 112 orthogonally intersects or otherwise intersects the core axis of the first setting block 114. The fluid is aspirated by an aspirating pump (not shown in the drawing) connected with the downstream portion of the outlet 119 and thereby flows from the inlet 118 to the outlet 119. The portion where the laser light La and the flow path 112 intersect is a particle detecting region 120.

The light receiving portion is comprised of a condenser lens for condensing scattered light Ls which is generated at the particle detecting region 120, a photodiode for photoelectrically converting the condensed scattered light Ls, and an amplifier. The light receiving portion receives scattered light Ls which is generated by irradiating the laser light La onto particles at the particle detecting region 120 in a case where the fluid contains particles, and outputs electrical signals depending on the intensity of the scattered light Ls.

The semiconductor laser 121 is attached to the second setting block 115 through a semiconductor laser setting member 128 having a heat sink 128a. A hole 128b having a larger diameter than that of a bolt 129 is formed in the semiconductor laser setting member 128. The semiconductor laser setting member 128 is attached to the second setting block 115 by twisting the bolt 129 into a threaded hole 115a formed in the second setting block 115 through the hole 128b.

In this instance, the optical axis of the semiconductor laser 121 is at least parallel to the optical axis of the laser medium 123. In order to make the optical axis of the semiconductor laser 121 and the optical axis of the laser medium 123 coincide with each other, the setting position of the semiconductor laser setting member 128 with respect to the second setting block 115 is adjusted by adjusting the position of the hole 128b and the bolt 129.

Therefore, the semiconductor laser setting member 128, the hole 128b formed in the semiconductor laser setting member 128, the threaded hole 115a formed in the second setting block 115, and the bolt 129 comprise a means for adjusting the setting position of the semiconductor laser 121.

The condenser lens 122 is attached to the second setting block 115 through an annular lens holder 130 having a penetrating hole 130a the diameter of which is substantially equal to the outside diameter of the condenser lens 122. The condenser lens 122 is set in the penetrating hole 130a of the lens holder 130.

An external thread is formed on the outer periphery surface of the lens holder 130, while an internal thread is formed on the inner periphery surface of the second setting block 115. As a result of this, the lens holder 130 is allowed to freely move in the direction of the optical axis of the condenser lens 122 with respect to the second setting block 115.

Figure 15:
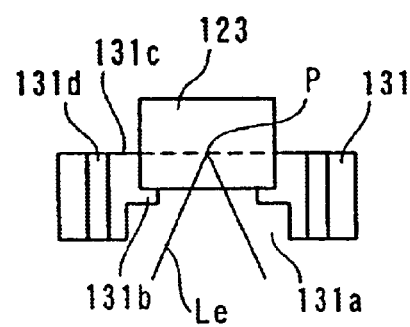
FIG. 15 is a view for explaining the incident condition of pumping laser light on a laser medium.

In this instance, the optical axis of the condenser lens 122 coincides at least with the optical axis of the laser medium 123. In order to make the condensing position of the pumping laser light Le using the condenser lens 122 coincide with the preferred position P in the laser medium 123 as shown in FIG. 15, the setting position of the condenser lens 122 is adjusted, which is conducted by turning the lens holder 130 with respect to the second setting block 115.

In addition, when the condensing position of the pumping laser light Le using the condenser lens 122 gets to the preferred position P in the laser medium 123, the top end of a lock bolt (not shown in the drawing) is made to abut against the outer periphery surface of the lens holder 130 by twisting the lock bolt into the threaded hole of the second setting block 115. As a result of this, the lens holder 130 is fixed to the second setting block 115, and thereby the setting position of the condenser lens 122 is determined.

Therefore, the second setting block 115 having an internal thread formed on the inner periphery surface thereof, the lens holder 130 having an external thread formed on the outer periphery surface thereof, the lock bolt, the threaded hole of the second setting block 115 into which the lock bolt is twisted, or the like comprise a means for adjusting the setting position of the condenser lens 122.

As the laser medium 123, for example, Nd:YVO$_4$, Nd:YAG, or the like can be used. At the end surface of the laser medium 123 facing toward the condenser lens 122 are formed an antireflection coating through which the pumping wavelength of the semiconductor laser 121 (the optical pumping wavelength of the laser medium 123) can penetrate and a reflection coating which reflects the oscillating wavelength of the laser medium 123. At the end surface of the laser medium 123 facing toward the side of the reflecting mirror 124 is formed an antireflection coating that is antireflective with respect to the oscillating wavelength of the laser medium 123. The laser light La resonating between the laser medium 123 and the reflecting mirror 124 is perpendicular to the end surface of the laser medium 123.

The laser medium 123 is attached to the second setting block 115 through a laser medium setting member 131 of a substantially cylindrical shape having a large diameter hole 131a for passing the pumping laser light Le generated from the semiconductor laser 121 through the center thereof. The laser medium 123 abuts against a stage portion 131b formed in the laser medium setting member 131.

When the laser medium 123 abuts against a stage portion 131b and thereby the laser medium 123 is set in the laser medium setting member 131, a surface 131c of the laser medium setting member 131 coincides with the preferred position P in the laser medium 123 to which the pumping laser light Le is condensed as shown in FIG. 15.

The irradiation port of the laser medium 123 which is on the optical axis (the irradiation direction of the laser light La) of the laser medium 123 is arranged to be on the core axis of the laser medium setting member 131. Also, the core axis of the laser medium setting member 131 and the core axis of the second setting block 115 are arranged to coincide with each other.

The reflecting mirror 124 is attached to the first setting block 114 through a reflecting mirror setting member 132. In this instance, the center of the reflecting surface which is on the optical axis (the reflection direction of the laser light La) of the reflecting mirror 124 is arranged to be on the core axis of the reflecting mirror setting member 132. Also, the core axis of the reflecting mirror setting member 132 and the core axis of the first setting block 114 are arranged to coincide with each other.

The fixation adjustment of the ninth embodiment of a light scattering type particle detector according to the present invention having the above-mentioned structure will be described hereinafter.

Figure 16:
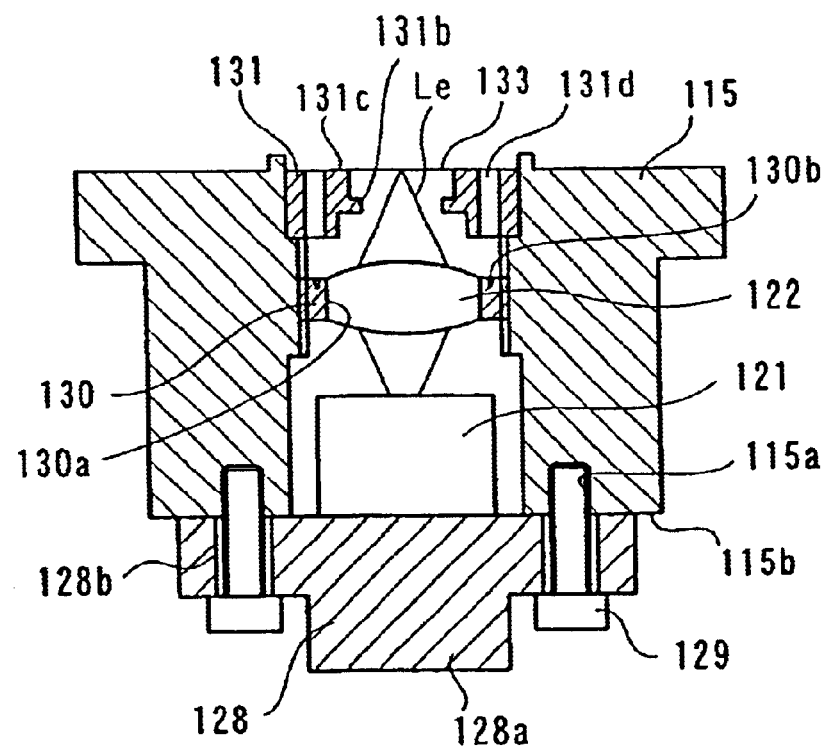
FIG. 16 is a cross-sectional view showing a schematic structure of a setting position adjusting means for a semiconductor laser and a schematic structure of a setting position adjusting means for a condenser lens.

First, as shown in FIG. 16, a subassembly is prepared in which the semiconductor laser 121 and the condenser lens 122 are fixed to the second setting block 115 and a semitransparent screen 133 having lines drawn longitudinally and transversely at equal intervals is set to the surface 131c of the laser medium setting member 131 instead of the laser medium 123. The optical axis of the condenser lens 122 and the center of the screen 133 coincide with each other.

Since the laser medium setting member 131 is provided so that the preferred position P in the laser medium 123 to which the pumping laser light Le is condensed coincides with the surface 131c of the laser medium setting member 131 as shown in FIGS. 15 and 16, the setting position of the screen 133 also coincides with the preferred position P.

Next, the subassembly is set to a jig for the fixation adjustment (not shown in the drawing).

The condensing position of the pumping laser light Le with the condenser lens 122 is adjusted to coincide with the preferred position P in the laser medium 123, which is conducted by moving the lens holder 130 to which the condenser lens 122 is set, so as to make the radiant of the pumping laser light Le condensed with the condenser lens 122 smallest where it falls on the screen 133. In this instance, the top end of the lock bolt is separated from the outer periphery surface of the lens holder 130.

Figure 17:
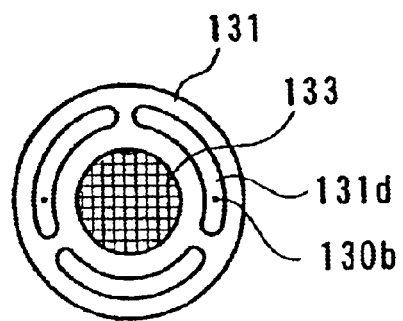
FIG. 17 is a plane view showing the condition where a screen is set in the laser medium setting member.

In order to move the lens holder 130, as shown in FIG. 17, an operation pin (not shown in the drawing) is inserted into the concave portion 130b formed in the end surface of the lens holder 130 via three arc-shaped elongated holes 131d formed around the large diameter hole 131a of the laser medium setting member 131.

The operation pin is moved in the direction to which the lens holder 130 is intended to be oriented, the lens holder 130 is rotated with respect to the second setting block 115, and the condenser lens 122 is moved to the direction of the optical axis thereof.

By moving the condenser lens 122, the radiant of the pumping laser light becomes smallest where it falls on the screen 133, that is, the pumping laser light Le is condensed on the screen 133. Then, the lock bolt is further twisted into the threaded hole of the second setting block 115, the top end of the lock bolt is allowed to abut against the outer periphery surface of the lens holder 130, and the lens holder 130 is set to an appropriate position and fixed with respect to the second setting block 115.

Next, the optical axis of the semiconductor laser 121 is adjusted to coincide with the optical axis of the laser medium 123, which is conducted by two-dimensionally moving the semiconductor laser setting member 128 to which the semiconductor laser 121 is set while keeping the semiconductor laser setting member 128 abutting against the end surface 115b of the second setting block 115 so as to make the condensing position of the pumping laser light Le coincide with the center of the screen 133, which coincides with the optical axis of the laser medium 123, as shown in FIG. 17. In this instance, the bolt 129 is provisionally fastened.

By moving the semiconductor laser setting member 128 two-dimensionally, the setting position of the semiconductor laser setting member 128 with respect to the second setting block 115 is determined so that the condensing position of the pumping laser light Le coincides with the center of the screen 133. Then, the bolt 129 is further twisted into the threaded hole 115a of the second setting block 115, and the semiconductor laser setting member 128 is set to an appropriate position and fixed with respect to the second setting block 115.

The fixation adjustment of the semiconductor laser 121 and the condenser lens 122 are thereby finished.

Next, the screen 133 is removed from the laser medium setting member 131, and the laser medium 123 is made to abut against the stage 131b of the laser medium setting member 131 and fixed.

In addition, the first setting block 114 to which the reflecting mirror 124 and the light receiving portion are set and the subassembly of the second setting block 115 for which the above-mentioned fixation adjustment is finished are fixed to each other.

Finally, a light scattering type particle detector according to the present invention can be obtained in which the intensity distribution (mode) of the pumping laser light Le generated from the semiconductor laser 121 is superposed on the intensity distribution (mode) of the laser light La irradiated from the laser medium 123.

As a result of this, it is possible to obtain laser light La having high output required for detecting finer particles and thereby finer particles can be detected with high accuracy.

Figure 18:
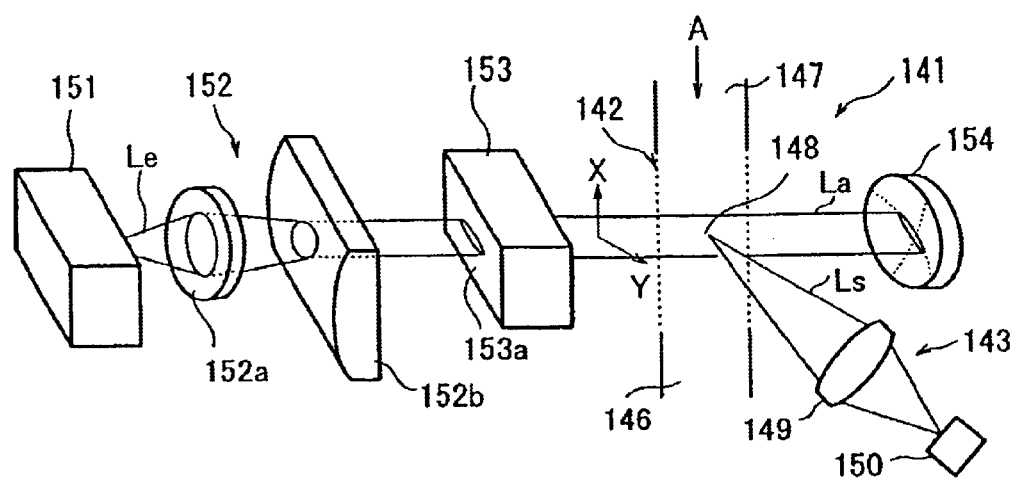
FIG. 18 shows a schematic structure of the tenth embodiment of a light scattering type particle detector according to the present invention.

The tenth embodiment of a light scattering type particle detector according to the present invention, as shown in FIG. 18, is comprised of a laser oscillator 141 as a light source, a flow path 142 which is defined by fluid to be detected, and a light receiving portion 143 for receiving scattered light Ls.

The laser oscillator 141 is comprised of a semiconductor laser 151 for generating pumping laser light Le having a circular transverse mode pattern, a condenser lens system 152 for condensing the pumping laser light Le, a solid-state laser 153 which is pumped by the pumping laser light Le condensed with the condenser lens system 152 and irradiates laser light La, and a concave mirror 154 for reflecting the laser light La which is irradiated from the solid-state laser 153 and allowing the reflected light to go back to the solid-state laser 153, which concave mirror 154 is provided to be opposed to the solid-state laser 153 in which the flow path 142 is provided therebetween.

The condenser lens system 152 is comprised of a convex lens 152a having a spherical shape and a cylindrical lens 152b. The laser light Le having a circular transverse mode pattern is condensed with the convex lens 152a, and thereafter it is converted into laser light having an elongated transverse mode pattern upon passing through the cylindrical lens 152b.

Laser light having an elongated transverse mode pattern refers to a condition where the cross-section of the laser beam has an elongated shape and specifically the laser beam is flattened to be short in the direction of the flow path 142 (hereinafter referred to as a X-direction) and long in the direction perpendicular to the flow path 142 (hereinafter referred to as a Y-direction).

As the solid-state laser 153, for example, Nd:YVO$_4$, Nd:YAG, or the like can be used. At the end surface of the solid-state laser 153 facing toward the the condenser lens system 152 are formed an antireflection coating through which the pumping wavelength of the semiconductor laser 151 (the optical pumping wavelength of the solid-state laser 153) can penetrate and a reflection coating which reflects the oscillating wavelength of the solid-state laser 153. At the end surface of the solid-state laser 153 facing toward the concave mirror 154 is formed an antireflection coating that is antireflective with respect to the oscillating wavelength of the solid-state laser 153.

The solid-state laser 153 emits laser light La having an elongated transverse mode pattern from the end surface thereof perpendicularly. In the same manner as the pumping laser light Le, the laser light La having an elongated transverse mode pattern refers to a condition where the cross-section of the laser beam has an elongated shape and specifically the laser beam is flattened to be short in the X-direction and long in the Y-direction.

The concave mirror 154 has a reflecting surface having a concave shape the radius of curvature of which is smaller in the X-direction than in the Y-direction. To the reflecting surface, a reflecting coating for reflecting the laser light La is coated. The optical axis of the concave mirror 154 is perpendicular to a surface 153a to which the reflection coating which reflects the oscillating wavelength of the solid-state laser 153 is coated.

The laser light La irradiated from the laser oscillator 141, that is, the laser light La oscillating between the solid-state laser 153 and the concave mirror 154 is kept in the condition of the elongated transverse mode pattern.

The flow path 142 is defined by fluid to be detected flowing from an inlet 147 to an outlet 146 in a direction shown by an arrow A in the drawing, the fluid being aspirated by an aspirating pump (not shown in the drawing) connected with the downstream portion of the outlet 146. The portion where the laser light La and the flow path 142 intersect is a particle detecting region 148.

Figure 19:
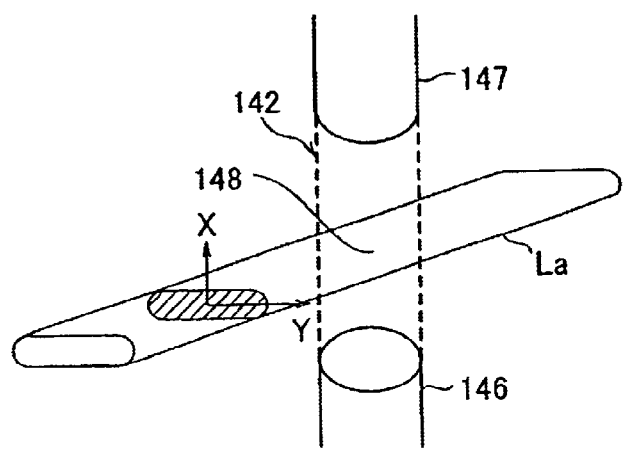
FIG. 19 is a perspective view showing the relationship between laser light and a flow path.

As shown in FIG. 19, by selecting the cylindrical lens 152b, it is possible to make the width of the laser light La in the Y-direction and the width of the flow path 142 coincide with each other. When the width of the laser light La in the Y-direction and the width of the flow path 142 coincide with each other, the whole cross section of the flow path 142 can be the particle detecting region 148 and thereby all particles passing through the flow path 142 can be detected. For example, if the cross section of the flow path 142 is a circular shape, it is possible to make the width of the laser light La in the Y-direction coincide with the diameter of the flow path 142.

The light receiving portion 143 is comprised of a condenser lens 149 for condensing scattered light Ls which is generated at the particle detecting region 148, a photodiode 150 for photoelectrically converting the condensed scattered light Ls, and so on. The light receiving portion 143 receives scattered light Ls which is generated by irradiating the laser light La onto particles at the particle detecting region 148 in a case where the fluid contains particles, and outputs electrical signals depending on the intensity of the scattered light Ls.

In the tenth embodiment of a light scattering type particle detector according to the present invention having the above-mentioned structure, when the transverse mode pattern of the laser light La irradiated from the laser oscillator 141 is of an elongated shape without varying the cross-sectional area of the laser light La, it is possible to broaden the width of the particle detecting region 148 without deteriorating the energy density (intensity) of the laser light La.

Also, by reducing the thickness in the X-direction, it is possible to control the increase in the volume of the particle detecting region, and thereby the increase of background light due to air molecules can be controlled and the increase of noise can also be controlled.

As shown in FIG. 19, when the width of the laser light La in the Y-direction and the width of the flow path 142 coincide with each other, the whole cross section of the flow path 142 can be the particle detecting region 148 and thereby all particles passing through the flow path 142 can be detected.

In addition, even if it is required to flow a great volume of sample fluid by increasing the cross-sectional area of the flow path 142, when the width of the laser light La in the Y-direction is broadened and the thickness of the laser light La in the X-direction is reduced to the extent that particles can be detected (the extent of the thickness of the laser light La in the X-direction), without varying the cross-sectional area of the laser light La it is possible to broaden the width of the particle detecting region 148 without deteriorating the energy density (intensity) of the laser light La.

Also, when the width of the laser light La in the Y-direction is broadened and the thickness of the laser light La in the X-direction is reduced to the extent that particles can be detected (the extent of the thickness of the laser light La in the X-direction) with varying reduction of the cross-sectional area of the laser light La, it is possible to broaden the width of the particle detecting region 148 and increase the energy density (intensity) of the laser light La.

Therefore, it is possible to flow a great volume of sample fluid through the flow path 142 and thereby a light scattering type particle detector which enables monitoring for high cleanness (low particle load) can be obtained.

Figure 20:
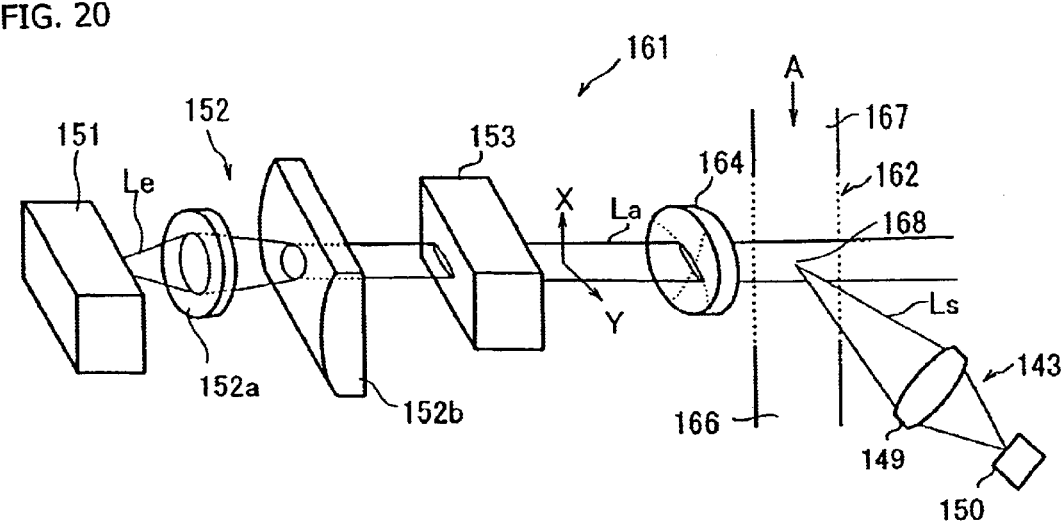
FIG. 20 shows a schematic structure of the eleventh embodiment of a light scattering type particle detector according to the present invention.

In the eleventh embodiment of a light scattering type particle detector according to the present invention, as shown in FIG. 20, a flow path 162 is provided outside a laser oscillator 161. In this case, since it is necessary to output laser light La to the outside of the laser oscillator 161, a semi-transparent mirror is used as a concave mirror 164. The concave mirror 164 has same functions as the concave mirror 154 shown in FIG. 18 except that the concave mirror 164 is a semi-transparent mirror.

The flow path 162 is defined by fluid to be detected flowing from an inlet 167 to an outlet 166 in a direction shown by an arrow A in the drawing, the fluid being aspirated by an aspirating pump (not shown in the drawing) connected with the downstream portion of the outlet 166. The portion where the laser light La and the flow path 142 intersect is a particle detecting region 168. The explanation of the elements having the same reference numbers as in FIG. 18 is omitted.

The light scattering type particle detector according to the eleventh embodiment having the above-mentioned structure has the same functions as the light scattering type particle detector shown in FIG. 18.

Figure 21:
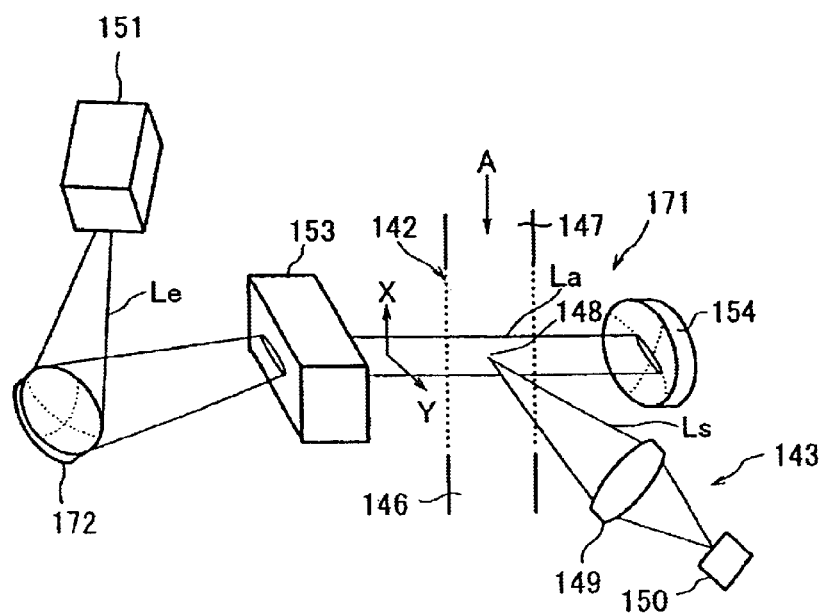
FIG. 21 shows a schematic structure of the twelfth embodiment of a light scattering type particle detector according to the present invention.
Figure 22:
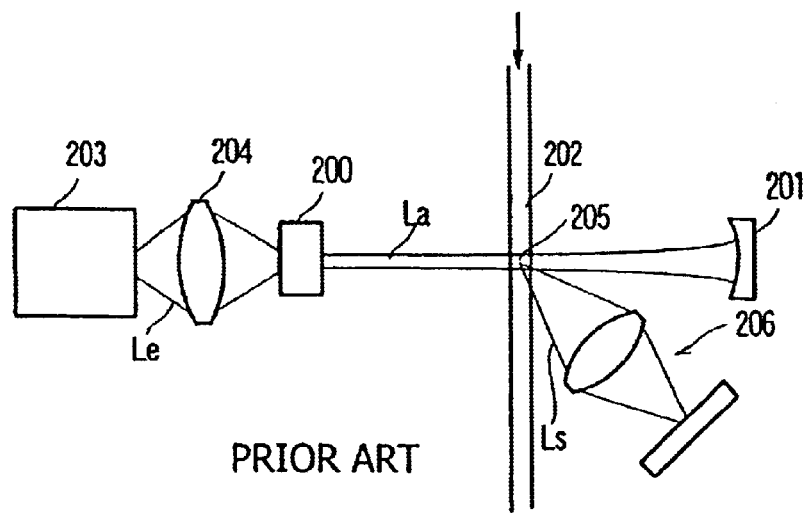
FIG. 22 shows a schematic structure of a conventional light scattering type particle detector.
Figure 23:
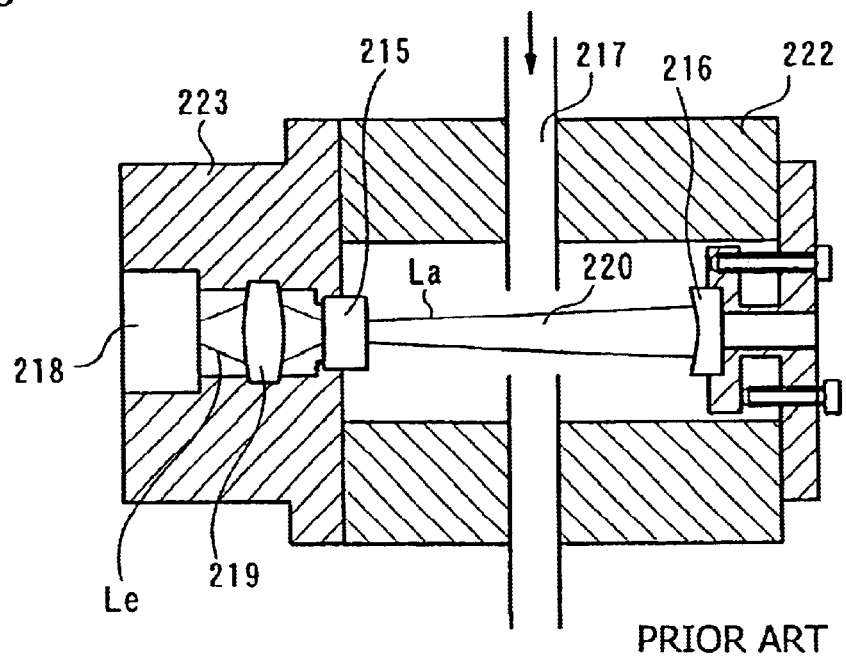
FIG. 23 is a cross-sectional view showing a schematic structure of another conventional light scattering type particle detector.
Figure 24:
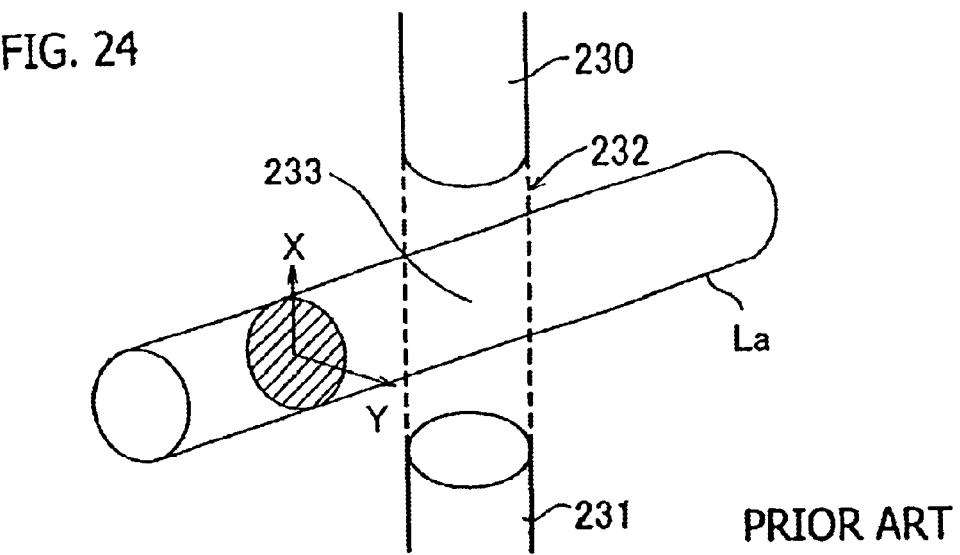
FIG. 24 is a perspective view showing the relationship between laser light and a flow path in the conventional light scattering type particle detector shown in FIG. 23.

In the twelfth embodiment of a light scattering type particle detector according to the present invention, as shown in FIG. 21, a laser oscillator 171 is provided so that pumping laser light Le generated from the semiconductor laser 151 is condensed with a concave mirror 172 and irradiated to a solid-state laser 153.

The concave mirror 172 has a reflecting surface having a concave shape the radius of curvature of which is different in the direction of the flow path 142 (X-direction) and the direction perpendicular to the flow path 142 (Y-direction). Pumping laser light Le having an elongated transverse mode pattern is irradiated to the solid-state laser 153 in the same manner as the condenser lens system 152 shown in FIG. 18. The explanation of the elements having the same reference numbers as in FIG. 18 is omitted.

The light scattering type particle detector according to the twelfth embodiment having the above-mentioned structure has same functions as the light scattering type particle detector shown in FIG. 18.

In the tenth, eleventh and twelfth embodiments, the pumping laser light Le generated from the semiconductor laser 151 is irradiated to the solid-state laser 153 on the condition that the cross section of the pumping laser light Le is made to have an elongated shape, the laser light is allowed to go back to the solid-state laser 153 with the concave mirrors 154 and 164 which have different radii of curvature in the parallel direction and the perpendicular direction with respect to the flow path, and thereby it is possible to obtain laser light La having an elongated transverse mode pattern.

However, it is also possible to obtain laser light La having an elongated transverse mode pattern by only making the transverse mode of pumping laser light Le generated from the semiconductor laser 151 an elongated shape. It is further possible to obtain laser light La having an elongated transverse mode pattern by making the laser light go back to the solid-state laser 153 with the concave mirrors 154 and 164, having reflecting surfaces of a concave shape, the radii of curvature of which are smaller in the X-direction than in the Y-direction.

What is claimed is:

1. A laser oscillator, comprising:
    a semiconductor laser for generating a pumping laser light;
    a laser medium for receiving said pumping laser light and for generating an attained laser light, said laser medium having an optical axis; and
    a concave mirror for reflecting pumping laser light from said semiconductor laser to said laser medium;
    wherein said pumping laser light generated from said semiconductor laser is condensed to irradiate upon said laser medium by said concave mirror, and wherein the said pumping laser light which is reflected by said concave mirror has a core axis which forms a predetermined non-linear angle with respect to the optical axis of said laser medium.

2. A light scattering particle detector for detecting particles contained in sample fluid which defines a flow path, said particle detector comprising a semiconductor laser and a concave mirror disposed between said flow path and said semiconductor laser, wherein laser light generated from said semiconductor laser is condensed to irradiate upon said flow path with said concave mirror and thereby a particle detecting region is defined; and an optical axis of said semiconductor laser and an optical axis of said concave mirror do not coincide.

3. The light scattering particle detector of claim 2, further comprising a condenser lens disposed between said flow path and said concave mirror and having an optical axis, and wherein the core axis of said laser light which is reflected by said concave mirror has a predetermined non-linear angle with respect to the optical axis of said condenser lens.

4. The light scattering particle detector of claim 2, wherein particles contained in said particle detecting region are detected by receiving scattered light generated by said laser light.

5. A light scattering particle detector comprising:

a semiconductor laser for generating pumping laser light;

a laser medium for being pumped by said pumping laser light;

a reflecting mirror on which laser light irradiated from said laser medium is reflected;

a flow path defined by sample fluid and being provided between said laser medium and said reflecting mirror; and a particle detecting region defined by irradiating said laser light to the flow path, said light scattering particle detector being adapted for detecting particles contained in said particle detecting region by receiving scattered light generated by said laser light, wherein the optical axis of said laser medium and the optical axis of said reflecting mirror are allowed to coincide with each other and a setting angle adjusting means is provided for adjusting setting angles of said laser medium and said reflecting mirror with respect to a setting block for each so as to make the optical axes intersect said flow path.

6. A light scattering particle detector according to claim 5, wherein said setting angle adjusting means comprises:

a laser medium setting member to which said laser medium is fixed, the setting angle of which laser medium setting member is adjustable with respect to said setting block for the laser medium;

a reflecting mirror setting member to which said reflecting mirror is fixed, the setting angle of which reflecting minor setting member is adjustable with respect to said setting block for the reflecting mirror; and elastic members which are interposed between said laser medium setting member and said setting block for the laser medium and between said reflecting mirror setting member and said setting block for the reflecting mirror.

7. A light scattering particle detector according to claim 6, wherein said elastic members are O-rings comprised of rubber.

8. A laser oscillator, comprising:

a semiconductor laser for generating a pumping laser light;

a laser medium for receiving said pumping laser light and for generating an attained laser light, said laser medium having an optical axis; and a condensing lens for directing condensed pumping laser light from said semiconductor laser to said laser medium;

wherein at least one of a setting position adjusting means for said semiconductor laser and a setting position adjusting means for the condenser lens is provided for superposing the intensity distribution of said pumping laser light generated from said semiconductor laser on the intensity distribution of said laser light irradiated from said laser medium.

9. A light scattering particle detector in which said laser light irradiated from said laser oscillator according to claim 8 is directed to a flow path defined by sample fluid, and thereby a particle detecting region is defined, particles contained in which particle detecting region are detected by receiving scattered light generated by irradiating said laser light onto said particles.

10. A laser oscillator in which pumping laser light generated from a pumping light source is condensed to irradiate upon a solid-state laser with a condenser and laser light irradiated from said solid-state laser is allowed to reflect back to said solid-state laser from a reflector, wherein at least one of said condenser and said reflector has a surface having different radii of curvature in the parallel direction and the perpendicular direction with respect to the flow path so that a cross-section of the laser light has an elongated shape flattened to be shorter in the direction of the flow path and longer in the direction perpendicular to the flow path.

11. A light scattering particle detector in which said laser light irradiated from said laser oscillator according to claim 10 is directed to a flow path defined by sample fluid, and thereby a particle detecting region is defined, and wherein particles contained in said particle detecting region are detected by receiving and analyzing scattered light generated by irradiating said laser light on said particles.

12. A laser oscillator in which pumping laser light generated from a semiconductor laser is condensed to irradiate upon a laser medium with a condenser lens, said laser mediums pumped, and thereby laser light is irradiated, wherein the optical axis of said semiconductor laser has a predetermined non-linear angle with respect to the optical axis of said laser medium.

13. A light scattering type particle detector in which said laser light irradiated from said laser oscillator according to claim 12 is condensed to irradiate upon a flow path defined by sample fluid, and thereby a particle detecting region is defined, particles contained wherein being detected by receiving scattered light generated by said laser light.

* * * * *

UNITED STATES PATENT AND TRADEMARK OFFICE
CERTIFICATE OF CORRECTION

PATENT NO. : 6,813,303 B2
DATED : November 2, 2004
INVENTOR(S) : Matsuda et al.

It is certified that error appears in the above-identified patent and that said Letters Patent is hereby corrected as shown below:

Column 27,
Line 9, change "minor setting member" to -- mirror setting member --.

Signed and Sealed this

Third Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,813,303 B2
APPLICATION NO. : 10/057779
DATED : November 2, 2004
INVENTOR(S) : Matsuda et al.

It is certified that error appears in the above-identified patent and that said Letters Patent is hereby corrected as shown below:

<u>Column 27,</u>
Line 54, change "minor setting member" to -- mirror setting member --.

This certificate supersedes Certificate of Correction issued May 3, 2005.

Signed and Sealed this

Twenty-fourth Day of October, 2006

JON W. DUDAS
*Director of the United States Patent and Trademark Office*